(12) United States Patent
Yamashita et al.

(10) Patent No.: US 6,300,368 B1
(45) Date of Patent: Oct. 9, 2001

(54) ANILIDE DERIVATIVES AND ANTIARRHYTHMIC AGENTS CONTAINING THE SAME

(75) Inventors: Hiroyuki Yamashita; Kazuhiko Togashi; Akiyoshi Kai; Junichi Mohri; Haruki Mori; Kohichi Kawai; Akihiro Oyabe; Takashi Sato, all of Chiba (JP)

(73) Assignee: Mitsui Chemicals, Inc. (JP)

( * ) Notice: Subject to any disclaimer, the term of this patent is extended or adjusted under 35 U.S.C. 154(b) by 0 days.

(21) Appl. No.: 09/340,022

(22) Filed: Jun. 28, 1999

(30) Foreign Application Priority Data

Jun. 30, 1998 (JP) .................................................. 10-184957

(51) Int. Cl.[7] .................. A61K 31/166; A61K 31/341; C07C 233/75; C07D 307/68; C07D 309/14
(52) U.S. Cl. .................... 514/459; 514/471; 514/617; 549/425; 549/487; 564/99; 564/176
(58) Field of Search .................................... 549/425, 487; 564/99, 176; 514/459, 471, 617

(56) References Cited

U.S. PATENT DOCUMENTS 3,898,278 * 8/1975 Ghelardoni et al. ................. 564/174
5,260,330 * 11/1993 Labisch et al. ....................... 514/428

FOREIGN PATENT DOCUMENTS

| 2923817 | 8/1980 | (DE) . |
| 4422517 | 1/1996 | (DE) . |
| 9901127 | 1/1999 | (WO) . |

OTHER PUBLICATIONS

Artini et al., Chemical Abstracts, 73:120262, 1970.*

* cited by examiner

*Primary Examiner*—Fiona T. Powers
(74) *Attorney, Agent, or Firm*—Burns, Doane, Swecker, & Mathis, L.L.P.

(57) ABSTRACT

Preparation of antiarrhythmic agents containing novel anilide derivatives represented by the following formula as active ingredient provides a new type of antiarrhythmic agent of highly safe and effective, without effects on cardiac function.

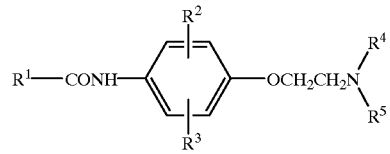

31 Claims, No Drawings

ANILIDE DERIVATIVES AND ANTIARRHYTHMIC AGENTS CONTAINING THE SAME

FIELD OF THE INVENTION

The present invention relates to novel anilide derivatives and antiarrhythmic agents containing them as an active ingredient.

DESCRIPTION OF THE RELATED ART

Cardiac arrhythmia can be divided into two large groups; ventricular and supraventricular arrhythmia. There are many antiarrhythmic agents already in market in order to suppress and prevent these arrhythmia. According to the classification system by Vaughan Williams, these agents can be classified into Class I suppressing the sodium channel in cardiac muscle, Class II being the β-blocker, Class III suppressing the potassium channel and Class IV suppressing calcium channel.

Ventricular arrhythmia sometimes causes severe blood circulation failure due to the function of ventricle to deliver blood to arteria and thus arrhythmia such as severe ventricular flutter and fibrillation is fatal. Therefore, a large scale clinical trials such as CAST (Cardiac Arrhythmia Suppression Trial) with Class I drugs such as Flecainide and Encainide and SWORD (Survival With Oral d-Sotalol Trial) with Class III drugs such as d-Sotalol in order to prove that prevention of ventricular arrhythmia results in decrease in mortality of patients.

However, results obtained indicated that treatment with these drugs make worse vital prognosis rather than placebo group and gave a warning for use of antiarrhythmic agents at random. Suppression of cardiac function by antiarrhythmic agents when they acted on ventricle and occurrence of new arrhythmia by effect of drugs so called proarrhythmia have been considered as a cause of such aggravation of vital prognosis. According to mode-of-action of existing antiarrhythmic agents, those belong to Classes I, II and IV essentially act on cardiac function as suppresser and those belong to Classes I and III pose a risk of proarrhythmia, therefore a new type of antiarrhythmic agent has been required.

On the other hand, supraventricular arrhythmia is very rare to become directly lethal, but in particular, atrial arrhythmia such as atrial flutter and fibrillation is very high in incidence, causes poor QOL (Quality of Life) problem because of giving strong subjective symptoms such as palpitation, gasping and heart pains, and could move to ventricular arrhythmia which endangers to one's life if it leaves without medical care. For chronic atrial fibrillation, it is well known that blood aggregate as a risk factor of cerebral thrombosis is readily formed due to intra-atrial congestion. Class I drugs are mainly used for atrial arrhythmia, and Class III drugs and Class II drugs may be used for atrial fibrillation associated with hypertrophic cardiomyopathy and sympathicotonic atrial fibrillation, respectively. However, antiarrhythmic agent which selectively acts on atria is not available, so that the same antiarrhythmic agents being used for ventricular arrhythmia are used for atrial arrhythmia.

Therefore, they also act on ventricle and have potential risks such as suppression of cardiac function, proarrhythmia and moreover aggravation of vital prognosis by chronic administration. These potential risks are serious problems because atrial arrhythmia itself is not lethal arrhythmia. Moreover, due to dose limitation to avoid side effect, suppression and prevention effects of atrial arrhythmia is not satisfactory for existing antiarrhythmic agents (Medicine and Drug Journal, Vol. 30, No. 9, 24–81, 1994).

Japanese Patent Laid-Open (Kokai) No. 125032/76 describes 4'-[2-(isopropylamino) ethoxy] acetanilide and 4'-[2-(cyclohexylamino) ethoxy] acetanilide as an example compound which are similar to the anilide derivatives having antiarrhythmic effect in the present invention. This document describes that these compounds act suppressively on ventricular function. In addition, these compounds differ from the anilide derivatives represented by Formula (1) in the present invention in the point that their $R^1$ is alkyl group.

SUMMARY OF THE INVENTION

An object to be solved according to the present invention is to provide a new type of antiarrhythmic agent free from ventricular function suppression and proarrhythmia and being highly safe.

As the results of active investigation conducted by the present inventors to achieve the above object, the present inventors have found that novel anilide derivatives having specific structure possess following pharmacological characteristics:

(1) Exhibit suppression and prevention effects of arrhythmia at dose levels from 0.3 to 10 mg/kg in aconitin-induced atrial fibrillation model and vagal atrial fibrillation model in anaesthetized dogs as well as in sterile pericarditis atrial flutter model in conscious dogs.

(2) Many compounds extend the effective refractory period of atria, but do not obviously affect on these of ventricle.

(3) Do not obviously affect on action potential in Purkinje's fiber in dogs.

(4) Do not obviously affect on cardiac blood circulation behavior and electrocardiogram in both anaesthetized and conscious dogs.

(5) Very weak side effect in acute toxicity and in central nervous system except for cardiac system.

Based on above findings, the present invention providing new type of antiarrhythmic agents free from effects on ventricular function and having superior effectiveness particularly to atrial arrhythmia has been completed.

Thus, the present invention relates to anilide derivatives expressed by formula (1):

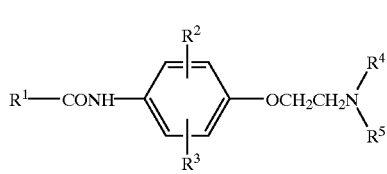

(1)

wherein:

$R^1$ represents a phenyl group (except for monoalkoxy phenyl group) having one or two substituents selected from $C_{1-3}$ alkoxy, $C_{1-3}$ alkyl, $C_{1-3}$ alkanesulfonamido and $C_{1-3}$ alkanesulfonyl groups, a furyl group, a 2,3,4,5-tetrahydrofuryl group, a 3,4,5,6-tetrahydro-2H-pyranyl group or —$(HC_2)_n OR^6$ (wherein, n represents an integral number 2 or 3, $R^6$ represents a $C_{1-4}$ alkyl group), $R^2$ and $R^3$ represent independently a hydrogen atom, a $C_{1-3}$ alkoxy group, a $C_{1-3}$ alkyl group, or a $C_{1-3}$ alkanesulfonamido group, $R^4$ and $R^5$ represent independently a hydrogen atom, a $C_{1-4}$ alkyl group, a $C_{3-6}$ cycloalkyl group, or —$(CH_2)_n OR^6$ (wherein, n represents an integral number 2 or 3, $R^6$ represents a $C_{1-4}$ alkyl group), or $R^4$ and $R^5$ together form —$(CH_2)_2W(CH_2)_2$— (wherein, W represents a direct bond, a methylene bridge or an oxygen atom); or their pharmacologically acceptable salts. The present invention relates also to antiarrhythmic agents containing one or more of the above anilide derivatives and their pharmacologically acceptable salts.

The present invention provides antiarrhythmic agents free from any effects on ventricular function. These antiarrhythmic agents are free from any risks such as cardiac function suppression and proarrhythmia, highly safe and particularly useful as therapeutic agent for atrial arrhythmia.

DETAILED DESCRIPTION OF THE INVENTION AND PREFERRED EMBODIMENTS

The present invention will be fully described below.

Compounds of the present invention represented by formula (1) are characterized in having anilide structure in the molecule with an amine side chain represented by —$OCH_2CH_2NR^4R^5$ attached to para-position thereof.

Regarding the substituents of the phenyl group as $R^1$ in formula (1), $C_{1-3}$ alkoxy groups include methoxy, ethoxy, propoxy and isopropoxy groups, $C_{1-3}$ alkyl groups include methyl, ethyl, propyl, isopropyl groups, $C_{1-3}$ alkanesulfonamido groups include methanesulfonamido, ethanesulfulfonamido, propanesulfonamido, and isopropanesulfonamido groups, $C_{1-3}$ alkanesulfonyl groups include methanesulfonyl, ethanesulfonyl, propane/sulfonyl, and isopropanesulfonyl groups. These substitutions can take place arbitrarily at one or two positions in phenyl group. However, the monoalkoxyphenyl group is excluded from the substituted phenyl group having only one alkoxy group, because its effect on the central nervous system is strong. Preferably, at least one of these substituents may substitute at the 2-position of the phenyl group, more preferably 2,6-dimethoxyphenyl, 2,6-diethoxylphenyl, 2,6-dimethylphenyl, substituted phenyl with $C_{1-3}$ alkanesulfonamido at the 2-position, and 2-(methanesulfonyl)phenyl groups, most preferably 2,6-dimethoxyphenyl, 2-(methanesulfonamido)phenyl, 2-(methanesulfonyl)phenyl groups.

Furyl group represented by $R^1$ of formula (1) is either 2-furyl or 3-furyl group, more preferably 3-furyl group. 2,3,4,5-Tetrahydrofuryl group represented by $R^1$ of formula (1) is either 2,3,4,5-tetrahydro-2-furyl or 2,3,4,5-tetrahydro-3-furyl, more preferably 2,3,4,5- tetrahydro-3-furyl. 3,4,5,6-Tetrahydro-2H-pyranyl group represented by $R^1$ of formula (1) is either 3,4,5,6-tetrahydro-2H-pyran-2-yl, 3,4,5,6-tetrahydro-2H-pyran-3-yl or 3,4,5,6-tetrahydro-2H-pyran-4-yl, more preferably 3,4,5,6-tetrahydro-2H-pyran-4-yl.

In —$(CH_2)_nOR^6$ (n represents an integral 2 or 3, $R^6$ represents $C_{1-4}$ alkyl group) represented by $R^1$ of formula (1), $R^6$ includes linear or branched alkyl groups such as methyl, ethyl, propyl, isopropyl, butyl, isobutyl, sec-butyl, tert-butyl groups, more preferably n is 2, most preferably 2-methoxyethyl group.

$C_{1-3}$ alkoxy groups represented by $R^2$ and $R^3$ include methoxy, ethoxy, propoxy, isopropoxy groups, $C_{1-3}$ alkyl groups include methyl, ethyl, propyl, isopropyl groups, $C_{1-3}$ alkanesulfonamido groups include methanesulfonamido, ethanesulfonamido, propanesulfonamido, isopropanesulfonamido groups. $R^2$ and $R^3$ can substitute at the arbitrary positions of 2', 3', 5', 6' in the benzene ring of the anilide (the position of substituent in the residual aniline of anilide derivatives is indicated by number with prime according to the IUPAC Organic Chemical Nomenclature Rule C-825.1). More preferably $R^2$ and $R^3$ are independently selected from hydrogen, methoxy, methyl, or methanesulfonamido group, most preferably $R^2$ is hydrogen and $R^3$ is selected from hydrogen, 3'-methyl, 3'-methoxy, or 3'-methanesulfonamido group, or $R^2$ is 3'-methyl and $R^3$ is 5'-methyl.

$C_{1-4}$ alkyl groups represented by $R^4$ and $R^5$ in formula (1) include linear or branched alkyl groups such as methyl, ethyl, propyl, isopropyl, butyl, isobutyl, sec-butyl, tert-butyl groups. $C_{3-6}$ cycloalkyl groups include cyclopropyl, cyclobutyl, cyclopentyl, cyclohexyl groups. When $R^4$ or $R^5$ represents —$(CH_2)_nOR^6$ (n is an integral 2 or 3, $R^6$ is $C_{1-4}$ alkyl), more preferably $R^6$ is methyl or ethyl group.

When $R^4$ and $R^5$ together form —$(CH_2)_2W(CH_2)_2$— (wherein, W represents a direct bond, a methylene bridge or an oxygen atom), a concrete example of —$NR^4R^5$ is 1-pyrrolidinyl, piperidino or morpholino group.

Particularly preferred amines represented by —$NR^4R^5$ are secondary amines in which $R^4$ represented by $C_{1-4}$ alkyl and $R^5$ represented by hydrogen.

In preferred embodiment, anilide derivatives represented by formula (1) may be

4'-[2-(ethylamino)ethoxy]-2-(methanesulfonamido) benzanilide,

4'-[2-(ethylamino)ethoxy]-2-(methanesulfonyl) benzanilide,

4'-[2-(ethylamino)ethoxy]-2,3,4,5-tetrahydro-3-furanilide,

4'-[2-(ethylamino)ethoxy]-3,4,5,6-tetrahydro-2H-pyran-4-carboxanilide,

4'-[2-(ethylamino) ethoxy]-3-methoxypropananilide,

4'-[2-(isopropylamino)ethoxy]-2,6-dimethoxybenzanilide,

4'-[2-(isopropylamino)ethoxy]-2-(methanesulfonamido) benzanilide,

4'-[2-(isopropylamino)ethoxy]-2-(methanesulfonyl) benzanilide,

4'-[2-(isopropylamino)ethoxy]-2,3,4,5-tetrahydro-3-furanilide,

4'-[2-(isopropylamino)ethoxy]-3,4,5,6-tetrahydro-2H-pyran-4-carboxanilide,

4'-[2-(isopropylamino)ethoxy]-3-methoxypropananilide,

4'-[2-(tert-butylamino)ethoxy]-2,6-dimethoxybenzanilide, 2-methanesulfonamido-4'-[2-[(2-methoxyethyl)amino] ethoxy]-benzanilide, 4'-[2-[(2-methoxyethyl)amino]ethoxy]-3-furanilide, 4'-[2-(ethylamino)ethoxy]-3'-methoxy-3-furanilide, 4'-[2-(isopropylamino)ethoxy]-2,6-dimethoxy-3'-methoxybenzanilide, 4'-[2-(isopropylamino)ethoxy]-2-methanesulfonyl-3'-methoxybenzanilide, 4'-[2-(isopropylamino) ethoxy]-3'-methoxy-3-furanilide, 4'-[2-(isopropylamino)ethoxy]-2-methanesulfonamide-3'-(methanesulfonamido)benzanilide, 4'-[2-(isopropylamino)ethoxy]-3'-methanesulfonamido-3-furanilide, 4'-[2-(isopropylamino)ethoxy]-2,6-dimethoxy -3'-methylbenzanilide, 4'-[2-(isopropylamino)ethoxy]-3'-methyl-3,4,5,6-tetrahydro-2H-pyran-4-carboxanilide, 4'-[2-(isopropylamino)ethoxy]-3- methoxy-3'-methylpropananilide, 4'-[2-(ethylamino)ethoxy]-2-methanesulfonamido-3',5'-dimethylbenzanilide, 4'-[2-(ethylamino)ethoxy]-2-methanesulfonyl-3',5'-dimethylbenzanilide, 4'-[2-(isopropylamino)ethoxy]-2-methanesulfonamido-3',5'-dimethylbenzanilide, 4'-[2-(isopropylamino)ethoxy]-2-methanesulfonyl-3',5'-dimethylbenzanilide, 4'-[2-(isopropylamino]ethoxy]-3-methoxy-3',5'-dimethylpropananilide.

If anilide derivatives represented by formula (1) are chiral compounds, not only racemic modifications and also optically active isomers are included.

Pharmacologically acceptable salts of said compounds are addition salts of inorganic acids such as hydrochloric acid, nitric acid, sulfuric acid, phosphoric acid, and further addition salts of organic acids such as acetic acid, oxalic acid, succinic acid, maleic acid, fumaric acid, lactic acid, malic acid, tartaric acid, methanesulfonic acid, p-toluenesulfonic acid, camphor sulfonic acid. Further, compounds having acidic groups such as an alkanesulfonamido group may be formed in salts with sodium, potassium and the like. Furthermore, the present invention includes hydrates and pharmacologically acceptable solvates.

Anilide derivatives represented by formula (1) of the present invention can be prepared according to general methods described below.

Anilide derivatives represented by formula (1) may be prepared by condensation reaction between carboxylic acid derivatives represented by formula (2)

$$R^1CO_2H \quad (2)$$

wherein, $R^1$ is the same as for formula (1). and aniline derivatives represented by formula (3)

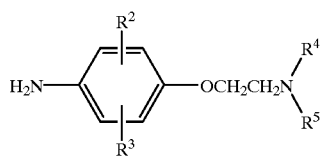
(3)

wherein, $R^2$, $R^3$, $R^4$ and $R^5$ are the same as for formula (1), using a condensing agent such as dicyclohexyl carbodiimide, carbonyl diimidazole, 2-chloro-1,3-dimethylimidazolium chloride, diphenylphosphoryl azide, cyanophosphoryl diethyl. Alternatively, carboxylic acid derivatives (2) may be converted to acid chloride, acid anhydride or activated ester thereof and then reacted with aniline derivatives (3). Inorganic bases such as sodium hydroxide, sodium hydrogen carbonate, potassium carbonate or tertiary-amines such as triethyl amine may be used as a deacidification agent if necessary when acid is formed as a by-product of the condensation reaction.

Aniline derivatives represented by formula (3) may be prepared by reducing nitro compounds represented by formula (4)

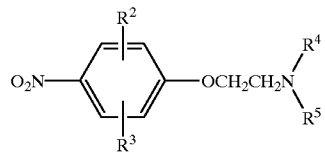
(4)

wherein, $R^2$, $R^3$, $R^4$ and $R^5$ are the same as for formula (1).

For reduction of the nitro group, a method using hydrogen in the presence of catalyst such as palladium, platinum, nickel, cobalt, or a reduction method by a metal such as iron, tin, zinc or tin(II)chloride may be used.

Nitro compounds represented by formula (4) may be prepared by several methods as described below.

Method 1:

The nitro compounds may be prepared by reacting compounds represented by formula (5)

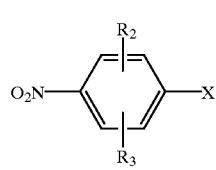
(5)

wherein, X represents fluorine, chlorine, bromine or iodide atom, $R^2$ and $R^3$ are the same as for formula (1), with metal aminoalkoxides represented by formula (6).

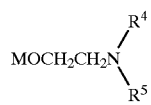
(6)

wherein, M represents lithium, sodium or potassium, $R^4$ and $R^5$ are the same as for formula (1).

Metal aminoalkoxide (6) may be generated in the original reaction vessel by reaction between corresponding amino alcohol and either lithium hydride, sodium hydride, potassium hydride, potassium tert-butoxide, lithium hydroxide, sodium hydroxide, potassium hydroxide, lithium carbonate, sodium carbonate, potassium carbonate or the like, and directly used without separating therefrom.

Method 2:

The nitro compounds may be prepared by reacting metal nitrophenoxides represented by formula (7)

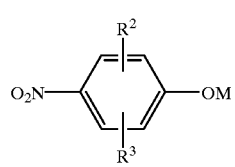
(7)

wherein, M represents lithium, sodium or potassium, $R^2$ and $R^3$ are the same as for formula (1), with compounds represented by formula (8),

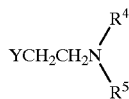
(8)

wherein, Y represents fluorine, chlorine, bromine, iodide, alkylsulfonyloxy or arylsulfonyloxy group, and $R^4$ and $R^5$ are the same as for formula (1).

Metal nitrophenoxides are sufficiently stable for use after separation from reaction mixture, but may be generated in the original reaction vessel by reaction between corresponding nitrophenol and either lithium hydride, sodium hydride, potassium hydride, sodium methoxide, potassium tert-butoxide, lithium hydroxide, sodium hydroxide, potassium hydroxide, lithium carbonate, sodium carbonate, potassium carbonate or the like and directly used without separating therefrom.

Method 3:

The nitro compounds may be prepared by reacting nitrophenol derivatives represented by formula (9)

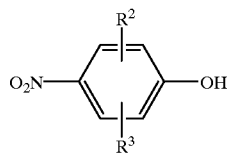
(9)

wherein, $R^2$ and $R^3$ are the same as for formula (1), with aminoalcohols represented by formula (10),

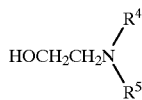
(10)

wherein, $R^4$ and $R^5$ are the same as for formula (1), under the presence of azo-dicarboxylic acid ester and triphenyl phosphine as condensation agents.

Method 4:

The nitro compounds may be prepared by reacting compounds represented by formula (11)

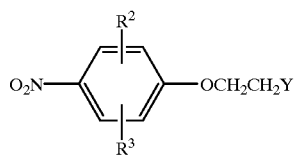
(11)

wherein, Y represents fluorine, chlorine, bromine, iodide, alkylsulfonyloxy or arylsulfonyloxy group, $R^2$ and $R^3$ are the same as for formula (1), with amines represented by formula (12),

(12)

wherein, $R^4$ and $R^5$ are the same as for formula (1).

Method 5:

The nitro compounds may be prepared by alkylation of the amino group in aminonitro compounds represented by formula (13)

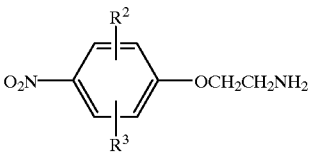
(13)

wherein, $R^2$ and $R^3$ are the same as for formula (1), with compounds represented by formula (14),

R—Y          (14)

wherein, R is the same as $R^4$ and $R^5$ in formula (1) and Y represents fluorine, chlorine, bromine, iodide, alkylsulfonyloxy or arylsulfonyloxy group.

Further, anilide derivatives represented by formula (1) may be prepared directly according to methods described above, using compounds as intermediate obtained by reducing in advance the nitro group in each compound represented by formula (5), (7), (9),(11) or (13) above and then by acylation with the carboxylic acid derivative (2) to convert thereof to $R^1CONH$ group.

The most suitable preparation method and reaction condition for the intended compound may be selected from above. The reaction may be performed by directly mixing all raw materials or by solubilizing or suspending all raw materials in an inert solvent appropriately selected from aqueous solvent, aromatic solvents such as toluene, alcohol solvents such as methanol, ether solvents such as dioxane, ester solvents such as ethyl acetate, amido solvents such as dimethyl formamido, halogenated solvents such as chloroform, ketone solvents such as acetone at reaction temperature in a range of 0 to 150° C. If it is necessary to heat up to temperature higher than the boiling point of the raw materials or solvent used, the reaction may be performed in an autoclave. If selectivity of reaction is required, tert-butoxycarbonyl, benzyloxycarbonyl, methoxycarbonyl, trimethylsilyl groups and the like may be used as a protecting group, if appropriate.

After collection by extraction, concentration or filtration, reaction product may be purified by procedures here-to-fore such as washing, distillation, crystallization, column chromatography.

Salts may be obtained according to procedures here-to-fore by dissolving or suspending the anilide derivatives into inactive solvent and by collecting precipitated salt with filtration or by removing solvent with concentration after addition of an appropriate acid or base into anilide solution.

Anilide derivatives according to the present invention may be administered by a method of oral dosages or as an injectable dose and the like to arrest arrhythmia or prevent recrudescence thereof.

As oral formulations, solid formulations such as tablets, pills, powders, granules, capsules and the like, and liquid formulations such as syrup, emulsifiable concentrate, suspension, aqueous liquid and the like may be selected according to the purpose of administration.

Solid formulations may include vehicles such as lactose, saccharose, salt, glucose, urea, starch, calcium carbonate, kaolin, microcrystalline cellulose and silica, binders such as water, ethanol, propanol, syrup, glucose solution, starch solution, gelatin solution, methyl cellulose solution, hydroxypropyl cellulose solution and carboxymethyl cellulose solution, disintegrators such as dried starch, sodium alginate, agar powder, sodium hydrogen carbonate, calcium carbonate, polyoxyethylenesorbitan fatty acid esters, sodium laurate, stearic glyceride and lactose, and lubricants such as talc, stearic acid salt, boric acid powder, polyethylene glycol as appropriate.

Tablet formulations my include sugar-coated tablet, gelatin capsule, enteric coated tablet, film-coated tablet, or double coated tablet and multilayered tablet, if appropriate.

Injectable formulations may include non-aqueous liquids utilized cotton seed oil, corn oil, peanut oil, olive oil, aqueous liquid utilizing physiological saline or glucose solution, or suspension and emulsifiable concentrate prepared by adding surfactant into aqueous suspension.

Infusion formulations may include aqueous solutions prepared utilizing physiological saline and glucose solution.

These formulations may include colorants, preservation stabilizers, aromatics, sweeteners and solubilizers if appropriate.

The dosage of the antiarrhythmic agent may be established depending on kind of arrhythmia, severity thereof, regimes, age and sex of patient, and other factors, however a suitable dosage range may usually be approximately 1 to 2000mg per adult per day as the active ingredient with once a day or divided into 2 to 3 times a day. The antiarrhythmic agents according to the present invention may be used in combination with any existing antiarrhythmic agents.

The present invention will now be illustrated by the following Examples, but is not restricted to these.

EXAMPLE 1

Preparation of 4'-(2-aminoethoxy)-2,6-dimethoxybenzanilide Hydrochloride (1-1) 4-Nitrophenol (4.01 g), 2-(tert-butoxycarbonylamino)ethanol (4.65 g) and triphenylphosphine (7.55 g) were dissolved into tetrahydrofuran (50 ml) and the solution was ice cooled. Azo dicarboxylic acid diethyl (5.52 g) dissolved in tetrahydrofuran (5 ml) was added drop-wise into the ice-cooled solution. After being stirred for one hour at room temperature, the reaction mixture was concentrated under vacuum. Residue was dissolved into ethyl acetate (50 ml). Hexane (400 ml) was added to the ethyl acetate solution and insoluble matter formed was removed from solution by filtration. Filtrate was concentrated under vacuum to small volume. Concentrate was purified by silica-gel column chromatography using ethyl acetate:hexane (1:1) as the solvent system to obtain N-(tert-butoxycarbonyl)-2-(4-nitrophenoxy)ethylamine (5.91 g) as color-less oily substance.

(1-2) N-(tert-butoxycarbonyl)-2-(4-nitrophenoxy)ethylamine (5.91 g) was dissolved into methanol (200 ml) and subjected to hydrogeration reaction at ambient pressure by adding 10% palladium carbon catalyst (0.5 g). After completion of hydrogeration reaction, excess catalyst was removed by filtration. Filtrate was concentrated under vacuum to obtain N-(tert-butoxycarbonyl)-2-(4-aminophenoxy)ethylamine (5.07 g) as color-less oily substance. (1-3) N-(tert-butoxycarbonyl)-2-(4-aminophenoxy)ethylamine (1.00 g) was dissolved into pyridine (5 ml) and 2,6-dimethoxybenzoic acid chloride (0.87 g) was added into the solution. After being stirred for one hour, the reaction mixture was concentrated under vacuum and residue was dissolved into chloroform (30 ml). The solution was washed with 1N sodium hydroxide aqueous solution (30 ml) followed by saturated sodium chloride (30 ml). Solvent was distilled out and residue was purified by silica-gel column chromatography (ethyl acetate:hexane=1:1) to obtain 4'-[2-(tert-butoxycarbonylamino)ethoxy]-2,6-dimethoxybenzanilide (1.17 g) as white powder.

(1-4) 4'-[2-(tert-Butoxycarbonylamino)ethoxy]-2,6-dimethoxybenzanilide (1.17 g) was added with 4N HCl/dioxane (5 ml) and mixed for 6 hours at room temperature. The reaction mixture was concentrated under vacuum and residue was dissolved into chloroform (50 ml). The solution was washed with 1N sodium hydroxide aqueous solution (10 ml) followed by saturated sodium chloride (20 ml). After concentration under vacuum to small volume, the solution was subjected to purification by silica-gel column chromatography (chloroform methanol=4:1) to obtain 4'-(2-aminoethoxy)-2,6-dimethoxybenzanilide (0.74 g) as white powder.

(1-5) 4'-(2-Aminoethoxy)-2,6-dimethoxybenzanilide (0.74 g) was dissolved into ethanol (5 ml) and added with 1N HCl/ethanol (5 ml). The solution was added with diethyl ether (100 ml). The precipitate was collected and dried under vacuum to obtain 4'-(2-aminoethoxy)-2,6-dimethoxybenzanilide hydrochloride (0.73 g) as white powder.

$^1$H-NMR (270 MHz, DMSO-$d_6$): δ=3.21 (2H, t), 3.76 (6H, s), 4.15 (2H, t), 6.71 (2H, d), 6.94 (2H, d), 7.34 (1H, t), 7.66 (2H, d), 8.30 (2H, br), 10.07 (1H, s); Melting point: 253–254° C.

EXAMPLE 2

Preparation of 4'-[2-(diethylamino)ethoxy]-2,6-dimethoxybenzanilide Hydrochloride (2-1) 4-Nitrophenoxy sodium dihydrate (29.39 g), 2-(diethylamino)ethylchloride hydrochloride (25.60 g), potassium carbonate (30.17 g) and water (60 ml) were added into xylene (100 ml) and the mixture was heat-refluxed for 2 hours while mixing and continuously removing water by azeotropic distillation. After reaction, insolubles were removed by filtration. Filtrate was added with ethyl acetate (100 ml) and extracted 3 times with 1N HCl (100 ml). Aqueous layer was adjusted to pH 10 with 1N sodium hydroxide and oily substance separated was extracted 3 times with ethyl acetate (100 ml). Ethyl acetate solution was dehydrated with anhydrous magnesium sulfate and concentrated to obtain N,N-diethyl-2-(4-nitrophenoxy)ethylamine (28.19 g) as color-less oily substance.

(2-2) N,N-diethyl-2-(4-nitrophenoxy)ethylamine (28.19 g) was dissolved into methanol (300 ml) and subjected to hydration reaction at ambient pressure by adding 10% palladium carbon catalyst (1.5 g). After completion of hydration reaction, catalyst was removed by filtration. Filtrate was concentrated under vacuum to obtain N,N-diethyl-2-(4-aminophenoxy)ethylamine (24.25 g) as color-less oily substance.

(2-3) N,N-diethyl-2-(4-aminophenoxy)ethylamine (4.00 g) was added into 2,6-dimethoxybenzoic acid chloride (4.20 g) in pyridine (40 ml) in an ice bath. After stirred for one hour at room temperature, the reaction mixture was concentrated under vacuum and residue was dissolved into chloroform (50 ml). The solution was washed with 1N sodium hydroxide aqueous solution followed by water and then saturated sodium chloride (50 ml, each). Solvent was distilled out and residue was purified by silica-gel column chromatography (chloroform:methanol=25:1) to obtain 4'-[2-(diethylamino)ethoxy]-2,6-dimethoxybenzanilide (5.01 g) as color-less crystal.

(2-4) 4'-[2-(Diethylamino)ethoxy]-2,6-dimethoxybenzanilide (2.17 g) was dissolved into ethanol (20 ml) and added with 1N HCl/ethanol (12 ml) and then stirred. The reaction mixture was added with ethyl ether (100 ml) and insolubles precipitated were collected by filtration and dried under vacuum to obtain 4'-[2-(diethylamino)ethoxy]-2,6-dimethoxybenzanilide hydrochloride (2.29 g) as color-less crystal.

$^1$H-NMR (270 MHz, DMSO-d$_6$): δ=1.27 (6H, t), 3.23 (4H, q), 3.51 (2H, t), 3.76 (6H, s), 4.31 (2H, t), 6.72 (2H, d), 6.98 (2H, d), 7.36 (1H, t), 7.66 (2H, d); Melting point: 205–206° C.

EXAMPLE 3

Preparation of 4'-[2-(ethylamino)ethoxy]-3,4,5,6-tetrahydro-2H-pyran-4-carboxanilide Hydrochloride (3-1) 3,4,5,6-Tetrahydro-2H-pyran-4-carboxylic acid (10.0 g) solution in dimethylformamido (15 ml) was added drop-wise with carbonyl diimidazole (13.1 g) in dimethylformamido (65 ml) in an ice bath and the mixture was stirred for 30 minutes at room temperature. 4-Aminophenol (8.4 g) solution in dimethylformamido (20 ml) was added drop-wise to this mixture in ice bath and the mixture was stirred for 5 hours at room temperature. The reaction mixture was concentrated to small volume and further stirred after addition of 2N HCl (100 ml). Crystals formed were collected by filtration, washed with water and then dried under vacuum at 60° C. to obtain 4'-hydroxy-3,4,5,6-tetrahydro-2H-pyran-4-carboxanilide (13.5 g) as white crystal.

(3-2) 4'-Hydroxy-3,4,5,6-tetrahydro-2H-pyran-4-carboxanilide (13.5 g), ethylene carbonate (5.96 g) and tetrabutylammonium iodide (2.26 g) were combined and stirred for 2 hours at 166° C. After being cooled, the mixture was added with water (100 ml) and further mixed. Crystals formed were collected by filtration, washed with water and then dried under vacuum at 60° C. to obtain 4'-(2-hydroxyethoxy)-3,4,5,6-tetrahydro-2H-pyran-4-carboxanilide (14.5 g) as white crystal.

(3-3) 4'-(2-Hydroxyethoxy)-3,4,5,6-tetrahydro-2H-pyran-4-carboxanilide (5.7 g) solution in pyridine (50 ml) was added with p-toluenesulfonylchloride (4.92 g). The mixture was stirred for 6 hours at room temperature and allowed to stand for one night. The reaction mixture was concentrated under vacuum and dissolved into chloroform (50 ml). This solution was washed water (50 ml) two times. After concentrated under vacuum, the organic layer was added with methanol (50 ml) and mixed. Crystals formed were collected by filtration, washed with water and then dried under vacuum at 60° C. to obtain 4'-[2-(p-toluenesulfonyloxy)ethoxy]-3,4,5,6-tetrahydro-2H-pyran-4-carboxanilide (5.17 g) as yellowish crystal.

(3-4) 4'-[2-(p-Toluenesulfonyloxy)ethoxy]-3,4,5,6-tetrahydro-2H-pyran-4-carboxanilide (1.7 g) solution in dioxane (20 ml) was added with 70% ethylamine aqueous solution (1.63 ml) and stirred for 6 hours at 90° C. The reaction mixture was concentrated under vacuum and dissolved into 2N HCl (20 ml). This solution was washed with ethyl acetate (20 ml) two times. Aqueous layer was neutralized with 2N sodium hydroxide (20 ml). Solid formed was extracted with ethyl acetate (50 ml), washed with water and then dehydrated with anhydrous magnesium sulfate. After filtration, filtrate was concentrated under vacuum and purified with silica-gel column chromatography to obtain 4'-[2-(ethylamino)ethoxy]-3,4,5,6-tetrahydro-2H-pyran-4-carboxanilide (0.77 g) as white solid.

(3-5) 4'-[2-(Ethylamino)ethoxy]-3,4,5,6-tetrahydro-2H-pyran-4-carboxanilide (0.77 g) was suspended into methanol (5 ml) and 1N HCl/ethanol solution (3.95 ml) was added into this suspension. The compound dissolved completely and formed a uniform solution at once, but later on hydrochloride thereof was separated as crystals. Crystals were collected by filtration and washed with diethyl ether (10 ml), then dried under vacuum to obtain 4'-[2-(ethylamino)ethoxy]-3,4,5,6-tetrahydro-2H-pyran-4-carboxanilide hydrochloride (0.80 g) as white crystal.

$^1$H-NMR (90 MHz, DMSO-d$_6$): δ=1.24 (3H, t), 1.4–1.8 (4H,m), 2.5–2.8 (1H, m), 3.03 (2H, q), 3.2–3.5 (4H, m), 3.8–4.1 (2H, m), 4.23 (2H, d), 6.94 (2H, d), 7.57 (2H, d), 9.87 (1H, s); Melting point : 251° C.

EXAMPLE 4

Preparation of 4'-[2-(isopropylamino)ethoxy]-2,6-dimethoxy-3'-methoxybenzanilide Hydrochloride (4-1) 2-Methoxy-4-nitrophenol (10.2 g), ethylene carbonate (5.66 g) and tetrabutylammonium iodide (2.1 g) were mixed and stirred for 2 hours at 160° C. After being cooled, all solids were dissolved into chloroform (300 ml) and the solution was washed with water (300 ml) two times. The organic layer was dehydrated with anhydrous magnesium sulfate (10 g) and concentrated under vacuum to obtain 2-(2-methoxy-4-nitrophenoxy)ethanol (12.0 g) as yellowish solid.

(4-2) 2-(2-Methoxy-4-nitrophenoxy)ethanol (12.0 g) and triethylamine (8.9 g) were dissolved into chloroform (60 ml) and p-toluenesulfonyl chloride (12.3 g) was added into this solution. The solution was stirred for 9 hours at room temperature and allowed to stand for one night. The reaction mixture was washed with water (100 ml) two times and dehydrated with anhydrous sodium sulfate and then concentrated under vacuum to dryness to obtain 2-(2-methoxy-4-nitrophenoxy)ethyl p-toluenesulfonate (25.9 g) as yellowish solid.

(4-3) 2-(2-Methoxy-4-nitrophenoxy)ethyl p-toluenesulfonate (19.5 g) and 70% aqueous isopropylamine solution (15.7 g) were dissolved into dioxane (100 ml) and the mixture was stirred for 9 hours at 73° C. After being concentrated under vacuum, the reaction mixture was dissolved into 2N HCl (50 ml) and washed with ethyl acetate (50 ml) two times. Resulting aqueous layer was neutralized with 2N sodium hydroxide (50 ml) and then extracted with ethyl acetate (100 ml). The organic layer was dehydrated with anhydrous sodium sulfate and then concentrated under vacuum to almost dryness to obtain N-isopropyl-2-(2-methoxy-4-nitrophenoxy)ethylamine (9.29 g) as yellowish oil.

(4-4) N-isopropyl-2-(2-methoxy-4-nitrophenoxy) ethylamine (9.29 g) solution in methanol (100 ml) was added with 10% palladium carbon catalyst and subjected to hydrogenation reaction at ambient pressure. After completion of hydrogenation reaction, catalyst was removed by filtration. Filtrate was concentrated under vacuum to obtain 4-[2-(isopropylamino)ethoxy]-3-methoxyaniline (8.15 g) as yellowish oily substance.

(4-5) 4-[2-(Isopropylamino)ethoxy]-3-methoxyaniline (3.0 g) solution in dimethylformamide (25 ml) was added drop-wise with 2,6-dimethoxybenzoic acid chloride (3.22 g) in dimethylformamide (25 ml) in ice bath and the mixture was stirred for 2 hours at room temperature. After being concentrated under vacuum, the reaction mixture was dissolved into 2N HCl (50 ml) and washed with ethyl acetate (50 ml) two times. Resulting aqueous layer was neutralized with 2N sodium hydroxide and then extracted with ethyl acetate (100 ml). The organic layer was dehydrated with anhydrous sodium sulfate (10 g) and then concentrated under vacuum to remove solvent.

Concentrate obtained was purified by silica-gel column chromatography (chloroform:methanol=20:1) to obtain 4'-[2-(isopropylamino)ethoxy]-2,6-dimethoxy-3'-methoxybenzanilide (4.1 g) as white solid.

$^1$H-NMR (270 MHz, CDCl$_3$): δ=1.10 (6H, d), 2.87 (1H, m), 2.99 (2H, t), 3.84 (6H, s), 3.90 (3H, s), 4.11 (2H, t), 6:60 (2H, d), 6.87 (2H, s), 7.31 (1H, t), 7.43 (1H, s), 7.66 (1H, s).

(4-6) 4'-[2-(Isopropylamino)ethoxy]-2,6-dimethoxy-3'-methoxybenzanilide (1.0 g) solution in isopropylalcohol (5 ml) was added with 1N HCl/ethanol (3.9 ml) and the mixture was stirred. Crystals separated were collected by filtration, washed with isopropylalcohol (5 ml) and dried under vacuum to obtain 4'-[2-(isopropylamino)ethoxy]-2,6-dimethoxy-3'-methoxybenzanilide hydrochloride (1.04 g) as white crystal.

Melting point: 191.1° C.

EXAMPLE 5

Preparation of 4'-[2-(isopropylamino)ethoxy]-3'-methanesulfonamido-2-(methanesulfonyl) benzanilide Hydrochloride (5-1) 2-Fluoro-5-nitroaniline (15.7 g) solution in pyridine (100 ml) was added drop-wise with methanesulfonylchloride (17.2 g) in an ice bathing. After being stirred for 2 hours at room temperature, the reaction mixture was added with 2N sodium hydroxide (200 ml) and washed with hexane (200 ml) two times. 2N HCl (300 ml) was added into the resultant aqueous layer and solids separated were collected by filtration, washed with water and dried under vacuum to obtain 2'-fluoro-5'-nitromethanesulfonanilide (21.8 g) as brownish solid.

(5-2) 2-(Isopropylamino)ethanol (24,0 g) solution in dimethylformamide (70 ml) was added with potassium tert-butoxide (21.9 g) in an ice bathing. After being stirred for 1 hour at room temperature, the reaction mixture was cooled down to 5° C. and added drop-wise with 2'-fluoro-5'-nitromethanesulfonanilide (21.8 g) in dimethylformamide (30 ml). After being stirred for 3 hours at room temperature, the reaction mixture was added into ethyl acetate (500 ml) and solids formed were collected by filtration and washed with ethyl acetate (100 ml). Solids obtained were dissolved into water (200 ml) and the solution was adjusted to pH=7 with 2N HCl. Resultant crystals were collected by filtration, washed with water, and dried under vacuum to obtain 2'-[2-(isopropylamino)ethoxy]-5'-nitromethanesulfonanilide (26.1 g) as white crystal.

(5-3) 2'-[2-(Isopropylamino)ethoxy]-5'-nitromethanesulfonanilide (26.1 g) was dissolved into mixed solvents of methanol (200 ml) and ethyl acetate (200 ml) and subjected to hydrogenation reaction with 10% palladium carbon catalyst at ambient pressure. After completion of hydrogenation reaction, catalyst was removed by filtration. Filtrate was concentrated to dryness under vacuum to obtain 5'-amino-2'-[2-(isopropylamino)ethoxy] methanesulfonanilide (22 g) as brownish solid.

(5-4) 5'-Amino-2-[2-(isopropylamino)ethoxy] methanesulfonanilide (2.16 g) solution in pyridine (20 ml) was added into 2-methanesulfonylbenzoic acid chloride (1.64 g) solution in pyridine (20 ml) in an ice bath and the mixture was stirred for 2 hours at room temperature. After being concentrated under vacuum, the reaction mixture was purified by silica-gel column chromatography (chloroform:methanol=5:1) to obtain 4'-[2-(isopropylamino) ethoxy]-3'-methanesulfonamido-2-(methanesulfonyl) benzanilide (2.8 g) as amorphous solid.

(5-5) 4'-[2-(Isopropylamino)ethoxy]-3'-methanesulfonamido-2-(methanesulfonyl)benzanilide (1.6 g) was dissolved into ethanol (50 ml) and to this solution 1N HCl/ethanol (9 ml) was added in an ice bath. The mixture was stirred. Crystals separated were collected by filtration, washed with ethanol (5 ml) and dried under vacuum to obtain 4'-[2-(isopropylamino)ethoxy]-3'-methanesulfonamido-2-(methanesulfonyl)benzanilide hydrochloride (1.6 g) as white crystal.

$^1$H-NMR (90 MHz, DMSO-d$_6$): δ=1.33 (6H, d), 3.01 (3H, s), 3.10–3.60 (6H, m), 4.23 (2H, t), 7.08 (1H, d), 7.50–8.10 (6H, m), 8.80–9.40 (2H, m), 10.59 (1H, s); Melting point: 217° C.

EXAMPLE 6

Preparation of 4'-[2-(isopropylamino)ethoxy]-2-methanesulfonamido-3',5'-dimethylbenzanilide Hydrochloride (6-1) 2,6-Dimethyl-4-nitrophenol (20.0 g), ethylenecarbonate (14.1 g) and tetrabutylammonium iodide (5.4 g) were combined and stirred for 2 hours at 150° C. After being cooled, the solution was dissolved into chloroform (200 ml), washed with water (200 ml), dehydrated with anhydrous magnesium sulfate (15 g) and then concentrated under vacuum to dryness to obtain 2-(2,6-dimethyl-4-nitrophenoxy)ethanol (22 g) as yellowish solid.

(6-2) 2-(2,6-Dimethyl-4-nitrophenoxy)ethanol (22 g) was dissolved into chloroform (200 ml) and triethylamine (20 ml) was added into this solution. Further, p-toluenesulfonylchloride (24.5 g) solution in chloroform (100 ml) was added into this solution in an ice bath. After being stirred for 6 hours at room temperature, the reaction mixture was washed with water (150 ml), 1N HCl (150 ml) and then 1N sodium hydroxide (150 ml). After being dehydrated with anhydrous magnesium sulfate (20 g), the solution was concentrated under vacuum to remove chloroform and residue was dissolved into ethyl acetate (50 ml). Hexane (200 ml) was added into ethyl acetate solution and separated solids were collected by filtration. Solids were dried under vacuum to obtain 2-(2,6-dimethyl-4-nitrophenoxy)ethyl p-toluenesulfonate (21.6 g) as yellowish solid.

(6-3) 2-(2,6-Dimethyl-4-nitrophenoxy)ethyl p-toluenesulfonate (10.0 g) solution in dioxane (15 ml) was added with isopropylamine (10 ml) and the mixture was stirred for 3 hours in an autoclave at 80° C. After being concentrated, the reaction mixture was dissolved into ethyl acetate (50 ml) and extracted with 1N HCl (150 ml). Resultant aqueous layer was added with 1N sodium hydroxide (200 ml) and extracted with chloroform (200 ml). After being dehydrated with anhydrous magnesium sulfate (20 g), chloroform layer was concentrated under vacuum to dryness to obtain N-isopropyl-[2-(2,6-dimethyl-4-nitrophenoxy)] ethylamine (5.5 g) as yellowish solid.

(6-4) N-isopropyl-[2-(2,6-dimethyl-4-nitrophenoxy)] ethylamine (5.5 g) solution in methanol (70 ml) was subjected to hydrogenation reaction with 10% palladium carbon catalyst at ambient pressure. After completion of hydrogenation reaction, catalyst was removed by filtration. Filtrate was concentrated to obtain 4-[2-(isopropylamino) ethoxy]3,5-dimethylaniline (4.80 g) as pale brownish oil.

(6-5) 4-[2-(Isopropylamino)ethoxy]3,5-dimethylaniline (2.6 g) solution in dimethylformamido (15 ml) was added with 2-(methanesulfonamido)benzoyl chloride (3.0 g) and the mixture was stirred for 2 hours at room temperature. After being concentrated under vacuum, the reaction mixture was dissolved into chloroform (50 ml) and extracted with 1N sodium hydroxide (100 ml). Resultant aqueous layer was neutralized with 1N HCl (100 ml) and extracted with chloroform (150 ml). Chloroform layer obtained was concentrated and purified by silica-gel column chromatography (chloroform:methanol=10:1) to obtain 4'-[2-isopropylamino) ethoxy]-2-methanesulfonamido-3',5'-dimethylbenzanilide (2.15 g) as white solid.

(6-6) 4'-[2-Isopropylamino)ethoxy]-2-methanesulfonamido-3',5'-dimethylbenzanilide (2.5 g) was dissolved into a mixture of ethanol (8 ml) and methanol (15 ml), to this solution 1N HCl/ethanol (10 ml) was added. Then, ethylether (100 ml) was added into this mixture. Crystals separated were collected by filtration, washed with ethylether (20 ml) and dried under vacuum to obtain 4'-[2-(isopropylamino)ethoxy]-2-methanesulfonamido-3',5'-dimethylbenzanilide hydrochloride (1.98 g) as white crystal.

$^1$H-NMR (270 MHz, DMSO-$d_6$): δ=1.32 (6H, d), 2.28 (6H, s), 3.12 (3H, s), 3.35 (2H, t), 3.38 (1H, m), 4.01 (2H, t), 7.27–7.33 (1H, m), 7.40 (2H, s), 7.52–7.63 (2H, m), 7.86 (1H, d), 10.38 (1H, s); Melting point: 209.8–212.1° C.

According to the preparation methods described in Examples 1 to 6, following compounds used for Examples 7 to 87 and Reference 1 were further prepared.

EXAMPLE 7

4'-[2-(Dimethylamino)ethoxy]-2,6-diethylbenzanilide $^1$H-NMR (90 MHz, CDCl$_3$): δ=2.34 (6H, s), 2.72 (2H, t), 3.83 (6H, s), 4.06 (2H, t), 6.59 (2H, d), 6.90 (2H, d), 7.22–7.40 (1H, m), 7.55 (2H, d); Melting point: 173–175° C. (hydrochloride).

EXAMPLE 8

4'-[2-(Diethylamino)ethoxy]-2,6-diethoxybenzanilide Hydrochloride $^1$H-NMR (270 MHz, DMSO-$d_6$): δ=1.24 (6H, t), 1.27 (6H, t), 3.22 (4H, q), 3.50 (2H, t), 4.04 (4H, q), 4.34 (2H, t), 6.68 (2H, d), 6.95 (2H, d), 7.28 (1H, t), 7.64 (2H, d), 9.98 (1H, s), 10.21 (1H, br); Melting point: 158–159° C.

EXAMPLE 9

4'-[2-(Diethylamino)ethoxy]-2-(methanesulfonamido)benzanilide Hydrochloride $^1$H-NMR (270 MHz, DMSO-$d_6$): δ=1.29 (6H, t), 3.12 (3H, s), 3.22 (4H, q), 3.51 (2H, t), 4.04 (2H, t), 7.01 (2H, d), 7.29 (1H, m), 7.57 (2H, d), 7.68 (2H, d), 7.95 (2H, d), 10.48 (1H, d), 10.65 (1H , br); Melting point: 172–173° C.

EXAMPLE 10

4'-[2-(Diethylamino)ethoxy]-2-(ethanesulfon amido) benzanilide Hydrochloride $^1$H-NMR (270 MHz, DMSO-$d_6$): δ=1.21 (3H, t), 1.28 (6H, t), 3.17–3.27 (6H, m), 3.52 (2H, t), 4.37 (2H, t), 7.01 (2H, d), 7.25 (1H, t), 7.55–7.63 (2H, m), 7.67 (2H, d), 7.94 (1H, d), 10.47 (1H, br); Melting point: 132° C.

EXAMPLE 11

4'-[2-(Diethylamino)ethoxy]-2-(propanesulfonamido)benzanilide Hydrochloride $^1$H-NMR (270 MHz, DMSO-$d_6$): δ=0.93 (3H, t), 1.30 (6H, t), 1.69 (2H, dt), 3.14–3.27 (6H, m), 3.50 (2H, t), 4.40 (2H, t), 7.01 (2H, d), 7.22–7.28 (1H, m), 7.52–7.62 (2H, m), 7.67 (2H, d), 7.96 (1H, d), 10.50 (2H, br); Melting point: amorphous.

EXAMPLE 12

4'-[2-(Diethylamino)ethoxy]-2-(isopropanesulfonamido)benzanilide Hydrochloride $^1$H-NMR (270 MHz, DMSO-$d_6$); δ=1.26 (6H, d), 1.29 (6H, t), 3.24 (4H, q), 3.37 (1H, m), 3.51 (2H, t), 4.38 (2H, t), 7.01 (2H, d), 7.24 (1H, t), 7.52–7.58 (1H, m), 7.64–7.68 (3H, m), 7.96 (1H, m), 10.25 (1H, br), 10.51 (1H, s); Melting point: 173–174° C.

EXAMPLE 13

4'-[2- (Dipropylamino)ethoxy]-2,6-dimethoxybenzanilide $^1$H-NMR (90 MHz, CDCl$_3$): δ=0.88 (6H, t), 1.46 (4H,. q), 2.50 (4H, t), 2.86 (2H, t), 3.83 (6H, s), 4.03 (2H, t), 6.59 (2H, d), 6.87 (2H, d), 7.21–7.40 (1H, m), 7.55 (2H, d); Melting point: amorphous (hydrochloride).

EXAMPLE 14

4'-[2-(Dipropylamino)ethoxy]-2,6-dimethylbenzanilide $^1$H-NMR (90 MHz, CDCl$_3$): δ=1.01 (6H, t), 1.60–2.10 (4H, m), 2.38 (6H, s), 2.90–3.25 (4H, m), 3.44 (2H, br), 4.52 (2H, br), 6.84–7.63 (7H, m); Melting point: 212–214° C. (hydrochloride).

EXAMPLE 15

4'-[2-(Dipropylamino)ethoxy]-2,6-dimethoxybenzanilide $^1$H-NMR (90 MHz, CDCl$_3$): δ=1.04 (2H, d), 2.81 (2H, t), 3.05 (2H, m), 3.83 (6H, s), 3.90 (2H, t), 6.59 (2H, d), 6.87 (2H, d), 7.21–7.60 (5H, m); Melting point: 116–120° C. (hydrochloride).

EXAMPLE 16

2,6-Dimethoxy-4'-[2-(1-pyrrolidinyl)ethoxy] benzanilide $^1$H-NMR (90 MHz, CDCl$_3$): δ=1.73–1.88 (4H, br), 2.64 (4H, br), 2.89 (2H, t), 3.83 (6H, s), 4.11 (2H, t), 6.59 (2H, d), 6.90 (2H, d), 7.21–7.40 (1H, m), 7.55 (2H, d); Melting point: 136–140° C. (hydrochloride).

EXAMPLE 17

2-Methanesulfonamido-4'-[2-(1-pyrrolidinyl)ethoxy] benzanilide $^1$H-NMR (90 MHz, CDCl$_3$): δ=1.76–1.91 (4H, m), 2.65–2.79 (4H, m), 2.87–2.96 (2H, m), 3.04 (3H, s), 4.14 (2H, t), 6.88 (2H, d), 7.40–7.69 (4H, m), 7.73 (2H, d); Melting point: 221–222° C. (hydrochloride).

EXAMPLE 18

2,6-Dimethoxy-4'-(2-piperidinoethoxy)benzanilide $^1$H-NMR (90 MHz, CDCl$_3$): δ=1.20–1.80 (6H, br), 2.52 (4H, t), 2.76 (2H, t), 3.83 (6H, s), 4.10 (2H, t), 6.58 (2H, d), 6.88 (2H, d), 7.21–7.40 (1H, m), 7.55 (2H, d); Melting point: 114–118° C. (hydrochloride).

EXAMPLE 19

2,6-Dimethyl-4'-(2morpholinoethoxy)benzanilide $^1$H-NMR (90 MHz, CDCl$_3$): δ=2.35 (6H, s), 2.70 (4H, t), 2.91 (2H, t), 3.78 (4H, t), 4.18 (2H, t), 6.63–7.56 (7H, m); Melting point: 177–190° C. (hydrochloride).

EXAMPLE 20

4'-[(2-Ethylamino)ethoxy]-2,6-dimethoxybenzanilide Hydrochloride $^1$H-NMR (270 MHz, DMSO-d$_6$): δ=1.25 (3H, t), 3.03 (2H, q), 3.33 (2H, t), 3.78 (6H, s), 4.24 (2H, t), 6.72 (2H, d), 6.95 (2H, d), 7.34 (1H, t), 7.67 (2H, d), 9.08 (2H, br), 10.08 (1H, s); Melting point: 257–259° C.

EXAMPLE 21

4'-[(2-Ethylamino)ethoxy]-2-(methanesulfonamido) benzanilide Hydrochloride $^1$H-NMR (90 MHz, DMSO-d$_6$): δ=1.20 (3H, t), 2.80–2.97 (2H, m), 2.89 (3H, s), 3.19 (2H, t), 4.15 (2H, t), 6.83–6.97 (3H, m), 7.21–7.73 (4H, m), 7.95–8.16 (1H, m); Melting point: 205–207° C.

EXAMPLE 22

4'-[(2-Ethylamino)ethoxy]-2-(methanesulfonyl) benzanilide Hydrochloride $^1$H-NMR (270 MHz, DMSO-d$_6$): δ=1.25 (3H, t), 3.05 (2H, q), 3.34 (2H, t), 3.37 (3H, s), 4.24 (2H, t), 7.01 (2H, d), 7.63–7.88 (5H, m), 8.03 (1H, dd), 10.55 (1H, s); Melting point: 229–230° C.

EXAMPLE 23

4'-[(2-Ethylamino)ethoxy]-2,3,4,5-tetrahydro-3-furanilide Hydrochloride $^1$H-NMR (90 MHz, DMSO-d$_6$): δ=1.24 (3H, t), 2.06 (2H, q), 2.86–3.40 (5H, m), 3.61–4.03 (4H, m), 4.24 (2H, t), 6.93 (2H, d), 7.57 (2H, d), 9.13 (1H, br), 10.10 (1H, s); Melting point: >250° C.

EXAMPLE 24

4'-[(2-Ethylamino)ethoxy]-3-methoxypropananilide $^1$H-NMR (90 MHz, DMSO-d$_6$): δ=1.03 (3H, t), 2.43–2.64 (4H, m), 2.85 (2H, t), 3.25 (3H, s), 3.62 (2H, t), 3,9,6 (2H, t), 6.84 (2H, d), 7.49 (2H, d), 9.73 (1H, br); Melting point: 216–217° C. (hydrochloride).

EXAMPLE 25

4'-[(2-Ethylamino)ethoxy]-3-furanilide Hydrochloride $^1$H-NMR (270 MHz, DMSO-d$_6$): δ=1.25 (3H, t), 3.05 (2H, q), 3.30 (2H, t), 4.24 (2H, t), 6.98–7.01 (3H, m), 7.66 (2H, d), 7.76 (1H, t), 8.36 (1H, d), 9.96 (1H, s); Melting point: >270° C.

EXAMPLE 26

2,6-Dimethoxy-4'-[2-(propylamino)ethoxy] benzanilide $^1$H-NMR (90 MHz, CDCl$_3$): δ=0.95 (3H, t), 1.47–1.71 (2H, m), 2.70 (2H, t), 3.03 (2H, t), 3.84 (6H, s), 4.11 (2H, t), 6.59 (2H, d), 6.89 (2H, d), 7.22–7.41 (2H, m), 7.55 (2H, d); Melting point: 243–244° C. (hydrochloride).

EXAMPLE 27

4'-[2-(Propylamino)ethoxy]-2,3,4,5-tetrahydro-3-furanilide Hydrochloride $^1$H-NMR (90 MHz, DMSO-d$_6$): δ=0.92 (3H, t), 1.69 (2H, m), 2.06 (2H, q), 2.83–4.03 (9H, m), 4.25 (2H,t), 6.93 (2H, d), 7.57 (2H, d), 9.18 (1H, br), 10.10 (1H, s); Melting point: >250° C.

EXAMPLE 28

4'-[2-(Propylamino)ethoxy]-3,4,5,6-tetrahydro-2H-pyran-4-carboxanilide Hydrochloride $^1$H-NMR (90 MHz, DMSO-d$_6$): δ=0.93,(3H, t), 1.5–1.9 (6H, m), 2.4–2.7 (1H, m), 2.94 (2H, t), 3.2–3.5 (4H, m), 3.8–3.9 (1H, m), 3.9–4.1 (1H, m), 4.24 (2H, t), 6.94 (2H, d), 7.57 (2H, d), 9.86 (1H, s); Melting point: 255° C.

EXAMPLE 29

4'-[2-(Isopropylamino)ethoxy]-2-(methanesulfonamido) benzanilide Hydrochloride $^1$H-NMR (270 MHz, DMSO-d$_6$): δ=1.32 (6H, d), 3.13 (3H, s), 3.2–3.4 (3H, m), 4.34 (2H, t), 7.02 (2H, d), 7.26 (1H, t), 7.52–7.59 (2H, m), 7.73 (2H, d), 8.03 (2H, d), 9.35 (2H, br), 10.56 (1H, s), 10.61 (1H, s); Melting point: 192.2° C.

EXAMPLE 30

4'-[2-(Isopropylamino)ethoxy]-2,6-dimethoxybenzanilide $^1$H-NMR (90 MHz, CDCl$_3$): δ=1.15 (6H, d), 2.88–2.97 (1H, m), 3.03 (2H, t), 3.84 (6H, s), 4.11 (2H, t), 6.60 (2H, d), 6.90 (2H, d), 7.23–7.42 (2H, m), 7.56 (2H, d); Melting point: 216–217° C. (hydrochloride).

EXAMPLE 31

4'-[2-(Isopropylamino)ethoxy]-2,6-dimethylbenzanilide $^1$H-NMR (90 MHz, CDCl$_3$): δ=1.01 (6H, d), 2.38 (6H, s), 2.72–3.04 (3H, m), 4.07 (2H, t), 6.85–7.55 (7H, m); Melting point: 204–207° C. (hydrochloride).

EXAMPLE 32

4'-[2-(Isopropylamino)ethoxy]-2-(methanesulfonyl) benzanilide Hydrochloride $^1$H-NMR (270 MHz, DMSO-d$_6$): δ=1.30 (6H, d), 3.3–3 (2H, t), 3.37 (3H, s), 3.39 (1H, m), 4.27 (2H, t), 7.02 (2H, d), 7.64 (2H, d), 7.67–7.88 (3H, m), 8.03 (1H, d), 10.56 (1H, s); Melting point: >250° C.

EXAMPLE 33

4'-[2-(Isopropylamino)ethoxy]-2,3,4,5-tetrahydro-3-furanilide Hydrochloride $^1$H-NMR (90 MHz, DMSO-d$_6$): δ=1.28 (6H, d), 2.06 (2H, q), 3.08–4.03 (10H, m), 4.25 (2H, t), 6.94 (2H, d), 7.57 (2H, d), 10.06 (1H, br); Melting point: 230° C.

EXAMPLE 34

4'-[2-(Isopropylamino)ethoxy]-3,4,5,6-tetrahydro-2H-pyran-4-carboxanilide Hydrochloride $^1$H-NMR (90 MHz, DMSO-d$_6$): δ=1.28 (6H, d), 1.5–1.8 (4H, m), 2.4–2.7 (1H, m), 3.2–3.5 (5H, m), 3.8–3.9 (1H, m), 3.9–4.0 (1H, m), 4.24 (2H, t), 6.93 (2H, d), 7.57 (2H, d), 9.88 (1H, s); Melting point: >250° C.

EXAMPLE 35

4'-[2-(Isopropylamino)ethoxy]-3-furanilide Hydrochloride $^1$H-NMR (90 MHz, DMSO-d$_6$): δ=1.30 (6H, d), 3.27–3.70 (3H, m), 4.27 (2H, t), 6.95–7.05 (3H, m), 7.63–7.78 (3H, m), 8.39 (1H, s), 9.99 (1H, s); Melting point: 229.5° C.

EXAMPLE 36

4'-[2-(Isopropylamino)ethoxy]-3-methoxypropananilide Hydrochloride $^1$H-NMR (270 MHz, DMSO-d$_6$): δ=1.29 (6H, d), 2.52 (2H, d), 3.25 (3H, s), 3.31 (2H, t), 3.38 (1H, m), 3.61 (2H, t), 4.22 (2H, t), 6.95 (2H, d), 7.55 (2H, d), 9.95 (1H, s); Melting point: 217.3–218.3° C.

EXAMPLE 37

4'-[2-(Butylamino)ethoxy]-2,6-dimethoxybenzanilide $^1$H-NMR (90 MHz, CDCl$_3$): δ=0.94 (3H, t), 1.2–1.6 (4H, m), 2.70 (2H, t), 3.02 (2H, t), 3.84 (6H, s), 4.09 (2H, t), 6.59 (2H, d), 6.89 (2H, d), 7.22–7.41 (2H, m), 7.56 (2H, d); Melting point: 199–200° C. (hydrochloride).

EXAMPLE 38

4'-[2-(Isobutylamino)ethoxy]-2,6-dimethoxybenzanilide $^1$H-NMR (90 MHz, CDCl$_3$): δ=0.94 (6H, d), 1.6–1.9 (1H, m), 2.53 (2H, d), 3.02 (2H, t), 3.84 (6H, s), 4.10 (2H, t), 6.59 (2H, d), 6.89 (2H, d), 7.22–7.41 (2H, m), 7.56 (2H, d); Melting point: 209–210° C. (hydrochloride).

EXAMPLE 39

2,6-Dimethoxy-4'-[2-(tert-butylamino)ethoxy]benzanilide $^1$H-NMR (90 MHz, DMSO-d$_6$): δ=1.32 (9H, s), 3.2–3.4 (2H, m), 3.78 (6H, s), 4.12–4.40 (2H, m), 6.75 (2H, d), 6.95 (2H, d), 7.23–7.45 (1H, m), 7.67 (2H, d), 10.08 (1H, s); Melting point: 247° C. (hydrochloride).

EXAMPLE 40

2-Methanesulfonamido-4'-[2-(tert-butylamino)ethoxy]benzanilide $^1$H-NMR (90 MHz, DMSO-d$_6$): δ=1.34 (9H, s), 3.11 (3H, s), 3.31 (2H, t), 4.28 (2H, t), 7.02 (2H, d), 7.54–7.73 (5H, m), 7.92 (1H, d); Melting point: 253–254° C. (hydrochloride).

EXAMPLE 41

4'-[2-[(2-Methoxyethyl)amino]ethoxy]-2,6-dimethoxy Benzanilide $^1$H-NMR (90 MHz, CDCl$_3$): δ=2.8 4 (2H, t), 3.00 (21H, t), 3.36 (3H, s), 3.51 (2H, t), 3.82 (6H, s), 4.05 (2H, t), 6.58 (2H, d), 6.87 (2H, d), 7.20–7.59 (3H, m); Melting point: 180–181° C. (hydrochloride).

EXAMPLE 42

2-Methanesulfonamido-4'-[2-[(2-methoxyethyl)amino]ethoxy]benzanilide $^1$H-NMR (90 MHz, CDCl$_3$): δ=2.81–3.09 (4H, m), 3.04 (31H, s), 3.37 (3H, s), 3.53 (2H, t), 4.08 (2H, t), 6.92 (2H, d), 7.16–7.26 (2H, m), 7.46 (2H, d), 7.61–7.81 (2H, m) Melting point: 164–165° C. (hydrochloride).

EXAMPLE 43

4'-[2-[(2-Methoxyethyl)amino]ethoxy]-2,3,4,5-tetrahydro-3-furanilide Hydrochloride $^1$H-NMR (90 MHz, DMSO-d$_6$): δ=2.06 (2H, q), 3.08–4.03 (14H, m), 4.24 (2H, t), 6.92 (2H, d), 7.56 (2H, d), 9.16 (1H, br), 10.08 (1H, s); Melting point: 210° C.

EXAMPLE 44

4'-[2-[(2-Methoxyethyl)amino]ethoxy]-3-methoxy propananilide Hydrochloride $^1$H-NMR (90 MHz, DMSO-d$_6$): δ=3.18–3.40 (6H, m), 3.25 (3H, s), 3.55–3.72 (4H, m), 4.25 (2H, t), 6.91 (2H, d), 7.56 (2H, d), 9.20 (1H, br), 9.93 (1H, br); Melting point: 171–172° C.

EXAMPLE 45

4'-[2-[(2-Methoxyethyl)amino]ethoxy]-3-furanilide Hydrochloride $^1$H-NMR (270 MHz, DMSO-d$_6$): δ=3.22 (2H, t), 3.30 (3H, s), 3.38 (2H, t), 3.66 (2H, t), 4.27 (2H, t), 6.98–7.01 (3H, m), 7.66 (2H, d), 7.76 (1H, t), 8.37 (1H, s), 10.00 (1H, s); Melting point: 228–229° C.

EXAMPLE 46

4'-[2-[(2-Ethoxyethyl)amino]ethoxy]-2,6-dimethoxy Benzanilide $^1$H-NMR (90 MHz, CDCl$_3$): δ=1.22 (3H, t), 2.85 (2H, t), 3.01 (2H, t), 3.40–3.67 (4H, m), 3.83 (6H, s), 4.07 (2H, t), 6.59 (2H, d), 6.88 (2H, d), 7.22–7.47 (1H, m), 7.56 (2H, d); Melting point: 145–150° C. (hydrochloride).

EXAMPLE 47

4'-[2-[(2-Ethoxyethyl)amino]ethoxy]-2-(methane sulfonamido)benzanilide $^1$N-NMR (90 MHz, CDCl$_3$): δ=1.21 (3H, t), 2.90 (2H, q), 3.09 (31H, s), 3.56 (2H, t), 4.08 (2H, t), 6.92 (2H, d), 7.41–7.81 (61H, m); Melting point: 171–172° C. (hydrochloride).

EXAMPLE 48

2,6-Dimethoxy-4'-[2-[(3-methoxypropyl)amino]ethoxy]benzanilide $^1$H-NMR (90 MHz, CDCl$_3$): δ=1.74 (2H, m), 2.74 (2H, t), 2.97 (2H, t), 3.32 (3H, s), 3.45 (2H, t), 3.81 (6H, s), 4.04

(2H, t), 6.57 (2H, d), 6.86 (2H, d), 7.20–7.41 (2H, m), 7.54 (2H, d); Melting point: 162–163° C. (hydrochloride).

EXAMPLE 49

2-Methanesulfonamido-4'-[2-[(3-methoxypropyl)amino]ethoxy]benzanilide Hydrochloride $^1$H-NMR (90 MHz, DMSO-d$_6$): δ=1.85–2.09 (2H, m), 2.88–3.49 (6H, m), 3.12 (3H, s), 3.56 (3H, s), 4.27–4.40 (2H, m), 7.01 (2H, d), 7.23–7.39 (2H, m), 7.56–7.73 (4H, m), 7.95 (2H, d); Melting point: 189–190° C.

EXAMPLE 50

4'-[2-(Cyclopropylamino)ethoxy]-2,6-dimethoxybenzanilide $^1$N-NMR (90 MHz, CDCl$_3$): δ=0.41–0.48 (4H, m), 2.16–2.27 (1H, m), 3.08 (2H, t), 3.83 (6H, s), 4.07 (2H, t), 6.59 (2H, d), 6.89 (2H, d), 7.22–7.47 (2H, m), 7.56 (2H, d); Melting point: 210° C. (hydrochloride).

EXAMPLE 51

4'-[2-(Cyclopropylamino)ethoxy]-2,3,4,5-tetrahydro-3-furanilide Hydrochloride $^1$H-NMR (90 MHz, DMSO-d$_6$): δ=0.61–0.96 (4H, m), 2.06 (2H, q), 2.68–3.50 (4H, m), 3.61–4.03 (4H, m), 4.26 (2H, t), 6.93 (2H, d), 7.56 (2H, d), 9.42 (1H, br), 10.05 (1H, s); Melting point: 206° C.

EXAMPLE 52

4'-[2-(Cyclopropylamino)ethoxy]-3,4,5,6-tetrahydro-2H-pyran-4-carboxanilide Hydrochloride $^1$H-NMR (90 MHz, DMSO-d$_6$): δ=0.7–0.9 (4H, m), 1.5–1.8 (4H, m), 2.4–2.6 (1H, m), 2.6–2.9 (1H, br), 3.1–3.5 (4H, m), 3.8–3.9 (1H, m), 3.9–4.2 (1H, m), 4.24 (2H, t), 6.93 (2H, d), 7.55 (2H, d), 9.84 (1H, s); Melting point: 246° C.

EXAMPLE 53

4'-[2-(Cyclopropylamino)ethoxy]-3-methoxypropananilide $^1$H-NMR (90 MHz, DMSO-d$_6$): δ=0.28–0.43 (4H, m), 2.10–2.28 (1H, m), 2.52 (2H, t), 2.97 (2H, t), 3.29 (3H, s), 3.66 (2H, t), 6.81 (1H, d), 7.49 (1H, d), 9.64 (1H, br); Melting point: 189–190° C. (hydrochloride).

EXAMPLE 54

4-[2-(Cyclopentylamino)ethoxy]-2-(methanesulfonamido) Benzanilide $^1$H-NMR (90 MHz, DMSO-d$_6$): δ=1.01–1.23 (2H, m), 1.63–1.98 (6H, m) 2.93 (3H, s), 3.09–3.51 (3H, m), 4.19 (2H, t), 6.78–7.02 (3H, m), 7.34 (2H, d), 7.67 (2H, d), 7.97 (1H, d); Melting point: 231–232° C. (hydrochloride).

EXAMPLE 55

4'-[2-(Cyclohexylamino)ethoxy]-2,6-dimethoxybenzanilide $^1$N-NMR (90 MHz, CDCl$_3$): δ=1.2–2.0 (10H, m), 2.5–2.7 (1H, br), 3.06 (2H, t), 3.84 (6H, s), 4.11 (2H, t), 6.60 (2H, d), 6.90 (2H, d), 7.23–7.41 (2H, m), 7.56 (2H, d); Melting point: 233° C. (hydrochloride).

EXAMPLE 56

4'-[2-(Ethylamino)ethoxy]-3'-methoxy-3-furanilide Hydrochloride $^1$H-NMR (90 MHz, DMSO-d$_6$): δ=1.24 (3H, t), 2.80–3.40 (4H, m), 3.79 (3H, s), 4.22 (2H, t), 6.98–7.01 (2H, m), 7.26 (1H, d), 7.50 (1H, d), 7.78 (1H, t), 8.38 (1H, s)., 9.91 (1H, s); Melting point: 141° C.

EXAMPLE 57

4'-[2-(Isopropylamino)ethoxy]-3-methoxy-3-methoxypropananilide $^1$H-NMR (90 MHz, CDCl$_3$): δ=1.04 (3H, s), 1.12 (3H, s), 1.84 (1H, s), 2.60 (2H, t), 2.97 (2H, t), 3.42 (3H, s), 3.72 (2H, t), 3.83 (3H, s), 4.08 (2H, t), 6.82 (2H, d), 7.39 (1H, s), 8.25 (1H, br); Melting point: 201–203° C. (hydrochloride).

EXAMPLE 58

4'-[2-(Isopropylamino)ethoxy]-2-methanesulfonamido-3'-methoxybenzanilide $^1$N-NMR (270 MHz, DMSO-d$_6$): δ=1.22 (6H, d), 2.83 (3H, s), 3.23 (2H, t), 3.37 (1H, m), 3.79 (3H, s), 4.14 (2H, t), 6.74 (1H, t), 7.01 (1H, d), 7.13 (1H, d), 7.24 (1H, t), 7.35 (1H, d), 7.63 (1H, d), 7.98 (1H, d); Melting point: amorphous (hydrochloride).

EXAMPLE 59

4'-[2-(Isopropylamino)ethoxy]-2-methanesulfonyl-3'-methoxybenzanilide Hydrochloride $^1$N-NMR (270 MHz, DMSO-d$_6$): δ=1.29 (6H, d), 3.32 (2H, t), 3.37 (3H, s), 3.42 (1H, m), 3.80 (3H, s), 4.22 (2H, t), 7.05 (1H, d), 7.27 (1H, dd), 7.42 (1H, d), 7.68 (1H, d), 7.77 (1H, t), 7.85 (1H, t), 8.03 (1H, d), 10.56 (1H, s); Melting point: 175° C.

EXAMPLE 60

4'-[2-(Isopropylamino)ethoxy]-3'-methoxy-3-furanilide Hydrochloride $^1$H-NMR (270 MHz, DMSO-d$_6$): δ=3.30 (6H, d), 3.31 (2H, t), 3.42 (1H, m), 3.80 (3H, s), 4.22 (2H, t), 6.86–7.05 (2H, m), 7.30 (1H, dd), 7.50 (1H, d), 8.38 (1H, s), 10.00 (1H, s); Melting point: 196° C.

EXAMPLE 61

4'-[2-(Cyclopentylamino)ethoxy]-3'-methoxy-3-methoxypropananilide $^1$H-NMR (90 MHz, CDCl$_3$): δ=1.2–2.0 (8H, br), 2.60 (2H, t), 2.98 (2H, t), 3.1–3.2 (1H, m), 3.44 (3H, s), 3.73 (2H, t), 3.85 (3H, s), 4.10 (2H, t), 6.82 (2H, br), 7.39 (1H, br), 8.10 (1H, br); Melting point: 163–164° C. (hydrochloride).

EXAMPLE 62

4'-[2-(Cyclopentylamino)ethoxy]-2,6-dimethoxy-3'-methoxybenzanilide Hydrochloride $^1$H-NMR (90 MHz, DMSO-d$_6$): δ=1.4–2.1 (8H, br), 3.2–3.4 (3H, m), 3.75 (9H, s), 4.21 (2H, t), 6.72 (2H, d), 6.99 (1H, d), 7.17 (2H, m), 7.56 (1H, s), 10.09 (1H, s); Melting point: 190.6° C.

EXAMPLE 63

4'-[2-(Diethylamino)ethoxy]-2,6-dimethoxy-3-methoxybenzanilide $^1$H-NMR (270MHz, CDCl$_3$): δ=1.07 (6H, t), 1.27 (2H, t), 2.64 (4H, q), 2.91 (2H, t), 3.87 (6H, s), 3.95 (3, s), 4.08

(21H, t), 6.57–6.61 (21H, d), 6.82–6.92 (2H, m), 7.27–7.34 (1H, m), 7.46 (1H, br), 7.6 5 (1H, s); Melting point: 169–170° C. (hydrochloride).

EXAMPLE 64

4'-[2-(Isopropylamino)ethoxy]-2'-methanesulfonamido-2,6-dimethoxybenzaniide Hydrochloride $^1$H-NMR (270 MHz, DMSO-d$_6$): δ=1.29 (6H, d), 2.93 (3H, s), 3.34–3.44 (3H, m), 3.82 (6H, s), 4.26 (2H, t), 6.77 (2H, d), 6.96 (1H, d), 7.09 (1H, d), 7.40 (2H, t), 7.49 (2(2H, d), 8.27 (1H, s), 9.96 (1H, s); Melting point: 209.5–210.2° C.

EXAMPLE 65

4'-[2-(Isopropylamino)ethoxy]-3'-methanesulfonamido-2,6-dimethoxybenzanilide $^1$N-NMR (90 MHz, CDCl$_3$): δ=1.19 (6H, d), 3.2–3.4 (3H, m), 3.84 (6H, s), 4.16 (2H, t), 6.58 (2H, d), 6.98 (1H, d), 7.31 (2H, m), 7.52 (1H, br), 7.89 (1H, d); Melting point: 176–178° C.

EXAMPLE 66

4'-[2-(Isopropylamino)ethoxy]-2-methanesulfonamido-3'-(methanesulfonamido)benzanilide Hydrochloride $^1$H-NMR (90 MHz, DMSO-d$_6$): δ=1.31 (6H, d), 3.02 (3H, s), 3.13 (3H, s), 3.3–3.5 (3H, m), 4.32 (2H, br), 7.10 (1H, d), 7.30–7.37 (1H, m), 7.55–7.80 (4H, m), 7.90 (1H, d), 9.11 (1H, br), 10.24 (1H, br), 10.50 (1H, s); Melting point: 229–230° C.

EXAMPLE 67

4'-[2-(Isopropylamino)ethoxy]-3'-methanesulfonamido-3-furanilide Hydrochloride $^1$H-NMR (270 MHz, DMSO-d$_6$): δ=1.34 (6H, d), 3.01 (3H, s), 3.40 (2H, t), 3.43 (1H, m), 4.25 (2H, t), 7.01–7.17 (2H, m), 7.59–7.63 (1H, m), 7.76 (2H, t), 8.38 (1H, dd), 10.03 (1H, s); Melting point: amorphous.

EXAMPLE 68

4'-[2-(Cyclopentylamino)ethoxy]-2-methanesulfonamido-3'-(methanesulfonamido)benzanilide Hydrochloride $^1$H-NMR (90 MHz, DMSO-d$_6$): δ=1.82 –2.08(8H, m),2.90 (3H, s), 2.99 (3H, s), 3.26 (2H, t), 3.41–3.55 (1H, m), 4.20 (2H, t), 6.76–7.11 (2H, m), 7.23–7.57 (3H, m), 7.80 (1H, d), 7.95 (1H, d); Melting point: amorphous.

EXAMPLE 69

4'-[2-(Isopropylamino)ethoxy]-2,6-dimethoxy-2'-methyl benzanilide Hydrochloride $^1$N-NMR (270 MHz, DMSO-d$_6$): δ=1.29 (6H, d), 2.25 (3H, s), 3.33 (2H, t), 3.38 (1H, m), 3.79 (6H, s), 4.24 (2H, t), 6.72 (2H, d), 6.82–6.89 (2H, m), 7.25–7.37 (2H, m), 9.47 (1H, s); Melting point: amorphous.

EXAMPLE 70

4'-[2-(Isopropylamino)ethoxy]-2-methanesulfonamido-2'-methylbenzanilide Hydrochloride $^1$H-NMR (270 MHz, DMSO-d$_6$): δ=1.30 (6H, d), 2.24 (3H, s), 3.12 (3H, s), 3.34 (2H, t), 3.37 (1H, m), 4.28 (2H, t), 6.87–6.96 (2H, m), 7.26–7.32 (2H, m), 7.56–7.64 (2H, m), 8.01–8.27 (1H, m); Melting point: amorphous.

EXAMPLE 71

4'-[2-(Isopropylamino)ethoxy]-3-methoxy-2'-methylpropananilide $^1$H-NMR (90 MHz, CDCl$_3$): δ=1.06 (3H, s), 1.13 (3H, s), 2.21 (3H, s), 2.64 (2H, t), 2.88–3.03 (3H, m), 3.45 (3H, s), 3.74 (2H, t), 4.04 (2H, t), 6.62–6.83 (2H, m), 7.71 (1H, d), 8.10 (1H, br); Melting point: amorphous.

EXAMPLE 72

4'-[2- (Isopropylamino)ethoxy]-2'-methyl-3-furanilide Hydrochloride $^1$H-NMR (270 MHz, DMSO-d$_6$): δ=1.30 (6H, d), 2.20 (3H, s), 3.33 (2H, t), 3.39 (1H, m), 4.26 (2H, t), 6.83–6.97 (3H, m), 7.20 (1H, d), 7.75 (1H, t), 8.32 (1H, s); Melting point: 207–209° C.

EXAMPLE 73

4'-[2-(Diethylamino)ethoxy]-2- dimethoxy-2'-methyl Benzanilide $^1$H-NMR (270 MHz, CDCl$_3$): δ=1.08 (6H, t), 2.88 (3H, s), 2.58–2.68 (4H, m), 2.87 (2H, t), 3.83 (6H, s), 4.04 (2H, t), 6.61 (2H, d), 6.77–6.87 (2H, m), 7.14 (1H, br), 7.31 (1H, t), 7.76 (2H, d); Melting point: 209–2 10° C. (hydrochloride).

EXAMPLE 74

4'-[2-(Isopropylamino)ethoxy]-2,6-dimethoxy-3'-methylbenzanilide Hydrochloride $^1$H-NMR (270 MHz, DMSO-d$_6$): δ=1.31 (6H, d), 2.21 (3H, s), 3.35 (2H, t), 3.43 (1H, m), 3.76 (6H, s), 4.22 (2H, t), 6.71 (2H, d), 6.91 (1H, d), 7.34 (1H, t), 7.48–7.54 (2H, m), 10.01 (1H, s); Melting point: 216.2–217.2° C.

EXAMPLE 75

4'-[2-(Isopropylamino)ethoxy]-2-methanesulfonamido-3'-methylbenzanilide Hydrochloride $^1$H-NMR (270 MHz, DMSO-d$_6$): δ=1.32 (6H, d), 2.25 (3H, s), 3.12 (3H, s), 3.37 (2H, t), 3.40 (1H, m), 4.26 (2H, t), 6.98 (1H, d), 7.25–7.31 (1H, m), 7.45–7.59 (4H, m), 7.91 (1H, d); Melting point: 201.6–202.0° C.

EXAMPLE 76

4'-[2-(Isopropylamino)ethoxy]-2-methanesulfonyl-3'-methylbenzanilide Hydrochloride $^1$H-NMR (270 MHz, DMSO-d$_6$): δ=1.31 (6H, d), 2.24 (3H, s), 3.37–3.49 (6H, m), 4.25 (2H, t), 6.97 (1H, d), 7.46–7.51 (2H, m), 7.65–7.69 (1H, m), 7.72–7.87 (2H, m), 8.01–8.04 (1H, m), 10.48 (1H, s); Melting point: >260° C.

EXAMPLE 77

4'-[2-(Isopropylamino)ethoxy]-3'-methyl-3,4,5,6-tetrahydro-2H-pyran-4-carboxanilide Hydrochloride $^1$N-NMR (90 MHz, DMSO-d$_6$): δ=1.29 (6H, d), 1.5–1.8 (4H, m), 2.19 (3H, s), 2.4–2.6 (1H, m), 3.2–3.8 (5H, m), 3.8–3.9 (1H, m), 3.9–4.1 (1H, m), 4.20 (2H, t), 6.89 (1H, d), 7.38 (1H, d), 7.43 (1H, d), 9.73 (1H, s); Melting point: >270° C.

EXAMPLE 78

4'-[2-(Isopropylamino)ethoxy]-3-methoxy-3'-methylpropananilide Hydrochloride $^1$H-NMR (270 MHz, DMSO-$d_6$): δ=1.27 (3H, s), 1.34 (3H, s), 2.19 (3H, s), 2.51 (2H, t), 3.24 (3H, s), 3.32–3.67 (4H, m), 4.23 (2H, t), 6.88 (1H, d), 7.37–7.43 (2H, m), 9.15 (1H, br); Melting point: 167–168° C.

EXAMPLE 79

4'-[2-(Isopropylamino)ethoxy]-3'-methyl-3-furanilide Hydrochloride $^1$H-NMR (270 MHz, DMSO-$d_6$): δ=1.30 (6H, d), 2.23 (3H, s), 3.36 (2H, t), 3.42 (1H, m), 4.22 (2H, t), 6.93–6.98 (2H, m), 7.49–7.54 (2H, m), 7.76 (1H, t), 8.34 (1H, s), 9.88 (1H, s); Melting point: 229.5° C.

EXAMPLE 80

4'-[2-(Ethylamino)ethoxy]-2-methanesulfonamido-3',5'-dimethylbenzanilide Hydrochloride $^1$H-NMR (90 MHz, DMSO-$d_6$): δ=1.27 (3H, t), 2.28 (6H, s), 3.12 (3H, s), 2.9–3.5 (4H, m), 4.00 (2H, t), 7.41 (2H, s), 7.22–7.58 (3H, m), 7.89 (1H, d), 10.32 (1H, s), 10.36 (1H, s); Melting point: 209.5° C.

EXAMPLE 81

4'-[2-(Ethylamino)ethoxy]-2-methanesulfonyl-3',5'-dimethylbenzanilide Hydrochloride $^1$H-NMR (90 MHz, DMSO-$d_6$): δ=1.26 (3H, t), 2.27 (6H, s), 2.9–3.2 (2H, m), 3.36 (3H, s), 3.3–3.6 (2H, m), 3.99 (2H, t), 7.37 (2H, s), 7.66–8.07 (4H, m), 10.46 (1H, s); Melting point: >250° C.

EXAMPLE 82

4'-[2-(Isopropylamino)ethoxy]-2,6-dimethoxy-3',5'-dimethyl benzanilide Hydrochloride $^1$H-NMR (270 MHz, DMSO-$d_6$): δ=1.31 (6H, d), 2.25 (6H, s), 3.33 (2H, t), 3.43 (1H, m), 3.74 (6H, s), 3.97 (2H, t), 6.71 (2H, d), 7.30–7.38 (3H, m), 10.03 (1H, s); Melting point: 239–245° C.

EXAMPLE 83

4'-[2- (Isopropylamino)ethoxy]-2-methanesulfonyl-3',5'-dimethylbenzanilide Hydrochloride $^1$N-NMR (270 MHz, DMSO-$d_6$): δ=1.32 (6H, d), 2.28 (6H, s), 3.10–3.60 (6H, m), 4.04 (2H, t), 7.37 (2H, s), 7.50–8.10 (4H, m), 9.11 (1H, br), 10.46 (1H, s); Melting point: >250° C.

EXAMPLE 84

4'-[2-(Isopropylamino)ethoxy]-3',5'-dimethyl-2,3,4,5-tetrahydro-3-furanilide Hydrochloride $^1$H-NMR (90 MHz, DMSO-$d_6$): δ=1.31 (6H, d), 2.12 (2H, q), 2.23 (6H, s), 3.00–3.45 (4H, m), 3.60–4.10 (6H, m), 7.28 (2H, s), 9.92 (1H, s); Melting point: 233° C.

EXAMPLE 85

4'-[2-(Isopropylamino)ethoxy]-3',5'-dimethyl-3,4,5,6-tetrahydro-2H-pyran-4-carboxanilide Hydrochloride $^1$N-NMR (90 MHz, DMSO-$d_6$): δ=1.30 (6H, d), 1.5–1.8 (4H, m), 2.23 (6H, s), 2.4–2.5 (1H, m), 3.2–3.6 (5H, m), 3.8–4.0 (4H, m), 7.28 (2H, s), 9.73 (1H, s); Melting point: >270° C.

EXAMPLE 86

4'-[2-(Isopropylamino)ethoxy]-3-methoxy-3',5'-dimethyl propananilide Hydrochloride $^1$H-NMR (90 MHz, DMSO-$d_6$): δ=0.98 (3H, s), 1.05 (3H, s), 2.19 (6H, s), 2.74–2.90 (5H, m), 3.24 (3H, s), 3.53–3.80 (4H, m), 7.23 (2H, s), 9.66 (1H, br); Melting point: 176–178° C.

EXAMPLE 87

4'-[2-(Isopropylamino)ethoxy]-3',5'-dimethyl-3-furanilide Hydrochloride $^1$H-NMR (270 MHz, DMSO-$d_6$): δ=1.32 (6H, d), 2.27 (6H, s), 3.39 (2H, t), 3.42 (1H, m), 4.00 (2H, t), 6.99 (1H, t), 7.39 (2H, s), 7.76 (1H, t), 8.35 (1H, t), 9.87 (1H, s) Melting point: 248–251° C.

REFERENCE 1

4'-[2-(Isopropylamino)ethoxy]acetanilide Hydrochloride $^1$H-NMR (270 MHz, DMSO-$d_6$): δ=1.28 (6H, d), 2.02 (3H, s), 3.31 (2H, t), 3.37 (1H, m), 4.22 (2H, t), 6.94 (2H, d), 7.53 (2H, d), 9.94 (1H, s); Melting point: >250° C.

FORMULATION EXAMPLE 1

Tablet containing 4'-[2-(isopropylamino)ethoxy]-2,6-dimethoxybenzanilide hydrochloride as an active ingredient The compound 50 g, lactose 38 g, corn starch 35 g and microcrystalline cellulose 20 g were well mixed, then kneaded with water 100 ml containing hydroxypropylcellulose 5 g. The mixture was granulated and dried for 4 hours at 50° C. Granules obtained were well mixed with magnesium stearate 2 g and made into tablets in weight of 150 mg/tablet using a tablet machine. Formulation Example 2

Capsule containing 4'-[2-(isopropylamino)ethoxy]-2-(methanesulfonamido)benzanilide hydrochloride as an active ingredient The compound 50 g, lactose 38 g, corn starch 35 g, microcrystalline cellulose 20 g and magnesium stearate 2 g were well mixed, and filled into hard capsules at the rate of 300 mg/capsule using an encapsulation machine. Formulation Example 3

Granular formulation containing 4'-[2-(isopropylamino)ethoxy]-2-(methanesulfonamido) benzanilide hydrochloride as an active ingredient The compound 100 g, lactose 150 g, corn starch 140 g and microcrystalline cellulose 80 g were well mixed, then kneaded with water 400 ml containing hydroxypropylcellulose 20 g. The mixture was granulated and dried for 4 hours at 50° C. After being sieved through 12-mesh screen, resultant uniform granules were mixed with magnesium stearate 8 g to obtain granules Formulation Example 4

Injectable material containing 4'-[2-(isopropylamino) ethoxy]-2-(methanesulfonamido) benzanilide hydrochloride as an active ingredient was prepared.

The compound 0.1 g was dissolved into physiological saline 5 ml. The solution obtained was sterilized through filter and filled into ampoules to obtain injectable doses.

Pharmacological Trial 1: Evaluation of effectiveness in aconitin-induced atrial fibrillation model (dogs) Evaluation was performed according to K. Hashimoto (Jpn. J. Pharmacol., Vol. 46, 349–358, 1988) as follows:

Method: Dog was anesthetized and thoracotomy was made. Persistent atrial fibrillation was induced by placing a piece of filter paper impregnated with 0.5% aconitin solution (20 to 30 μl) on the right atrium. Test substance dissolved into physiological saline was intravenously administered to dogs exhibiting atrial fibrillation and the minimum dose level which suppresses atrial fibrillation was determined. Onset and suppression of atrial fibrillation were monitored electrocardiographically by placing Ag—AgCl bipolar electrode on the right atrial auricle.

Results: Each compound in Examples 1 to 87 suppressed atrial fibrillation at least following dose level (all compounds were used in the form of hydrochloride).

Compounds suppressed atrial fibrillation at the dose level of 0.3 mg/kg
Compounds in Examples 29, 40 and 55
Compounds suppressed atrial fibrillation at the dose level of 10 mg/kg
Compounds in Examples 2, 3, 4, 5, 6, 8, 9, 13, 15, 16, 17, 18, 21, 24, 25, 26, 30, 31, 32, 33, 35, 36, 39, 41, 45, 46, 49, 53, 54, 56, 57, 58, 59, 60, 61, 62, 63, 64, 65, 67, 68, 75, 77, 79, 82, 83 and 87
Compounds suppressed atrial fibrillation at the dose level of 3.0 mg/kg
Compounds in Examples 7, 10, 11, 12, 14, 19, 22, 23, 27, 28, 34, 37, 38, 42, 47, 48, 50, 51, 52, 66, 69, 70, 71, 72, 73, 74, 76, 78, 80, 81 and 86
Compounds suppressed atrial fibrillation at the dose level of 10 mg/kg
Compounds in Examples 1, 20, 43, 44, 84 and 85

Pharmacological Trial 2: Evaluation of Effects on Ventricle

Method: Purkinje's fiber specimen excised from the right ventricular free wall of dog, perfused with normal Tyrode solution and driven by electrical stimulation (fundamental frequency=1 Hz) was used. Standard glass microelectrode was used to record action potential. After measurement of the maximum rate of rise for action potential (Vmax), duration to repolarize 50% (APD50), 75% (APD75) and 90% (APD90), Tyrode solution was replaced by Tyrode solution spiked with test or reference substance and again the same parameter was measured.

Results: All compounds in Examples 1 to 87 (used as hydrochloride) did not affect on action potential of Purkinje's fiber with less than 10% of changes at the concentration of 30 μM.

On the other hand, representative existing antiarrhythmic agents Flecanide (Class Ic) suppressed Vmax by 30% at 3 μM and Disopyramido (Class Ia) suppressed Vmax by 33% at 30 μM. Dofetilide (Class III) extended APD50, APD75 and APD90 by 57, 45 and 42%, respectively, at the concentration of 10 μM. 4'-[2-(Isopropylamino)ethoxy]acetanilide hydrochloride referred here as Reference 1 and disclosed in Tokkai-Sho 51-125032 suppressed Vmax by 15% at concentration of 30 μM.

Thus, all compounds according to the present invention did not affect on ventricle, unlike existing drugs.

Pharmacological Trial 3: Safety evaluation by simple acute toxicity test in mice Method: Groups of three ddY male mice were dosed at single dose level of 50 mg/kg with intravenous injection of test substance solution in saline into caudal vein. Animals were observed for clinical signs for one hour after dosing and mortality was observed 48 hours after dosing.

Results: In all groups treated with test substances in Examples 1 to 87 (used as hydrochloride), no death nor any abnormal behavior was observed.

What is claimed is:

1. An anilide derivative represented by formula (1) or a pharmacologically acceptable salt thereof:

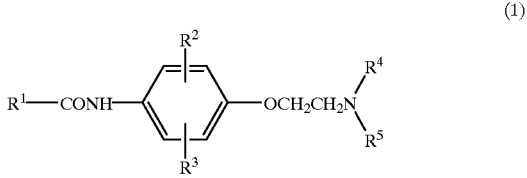

wherein
$R^1$ represents a phenyl group (except for monoalkoxy phenyl group and monoalkyl phenyl group) having one or two substituents selected from the group consisting of $C_{1-3}$ alkoxy groups, $C_{1-3}$ alkyl groups, $C_{1-3}$ alkanesulfonamido groups and $C_{1-3}$ alkanesulfonyl groups; a furyl group; a 2,3,4,5-tetrahydrofuryl group; a 3,4,5,6-tetrahydro-2H-pyranyl group; or —$(CH_2)_n OR^6$ (wherein, n represents an integral number 2 or 3 and $R^6$ represents a $C_{1-4}$ alkyl group), at either the 2-position or both of the 2-position and the 6-position, $R^2$ and $R^3$ represent independently a hydrogen atom, a $C_{1-3}$ alkoxy group, a $C_{1-3}$ alkyl group, or a $C_{1-3}$ alkanesulfonamido group, and $R^4$ and $R^5$ represent independently a hydrogen atom, a $C_{1-4}$ alkyl group, a $C_{3-6}$ cycloalkyl group, or —$(CH_2)_n OR^6$ (wherein, n represents an integral number 2 or 3, and $R^6$ represents a $C_{1-4}$ alkyl group).

2. The anilide derivative or pharmacologically acceptable salt thereof according to claim 1, wherein
$R^1$ represents a 2,6-dimethoxyphenyl group, a 2,6-diethoxyphenyl group, a 2,6-dimethylphenyl group, a 2,6-diethyphenyl group, a phenyl group substituted with a $C_{1-3}$ alkanesulfonamido group at the 2-position, a 2-(methanesulfonyl)phenyl group, a furyl group, a 2,3,4,5-tetrahydrofuryl group, a 3,4,5,6-tetrahydro-2H-pyranyl group or a 2-methoxyethyl group, $R^2$ and $R^3$ represent independently a hydrogen atom or a methoxy group, a methyl group or a methanesulfonamido group and $R^6$ represents a methyl group or an ethyl group.

3. The anilide derivative or pharmacologically acceptable salt thereof according to claim 2 wherein $R^1$ represents a 2,6-dimethoxyphenyl group, a 2-(methanesulfonamido)phenyl group, a 2-(methanesulfonyl)phenyl group, a 3-furyl group, a 2,3,4,5-tetrahydro-3-furyl group, a 3,4,5,6-tetrahydro-2H-pyran-4-yl group or a 2-methoxyethyl group.

4. The anilide derivative or pharmacologically acceptable salt thereof according to claim 3, wherein $R^4$ represents a $C_{1-4}$ alkyl group and $R^5$ represents a hydrogen atom.

5. The anilide derivative or pharmacologically acceptable salt thereof according to claim 4, wherein $R^2$ represents hydrogen atom and $R^3$ represents a hydrogen atom, a 3'-methyl group, a 3'-methoxy group or a 3'-methanesulfonamido group.

6. The anilide derivative or pharmacologically acceptable salt thereof according to claim 4, wherein $R^2$ represents a 3'-methyl group and $R^3$ represents a 5'-methyl group.

7. An antiarrhythmic agent comprising an excipient and the anilide derivative or pharmacologically acceptable salt thereof claimed in any one of claims 1 to 6 as active ingredient.

8. The anilide derivative or pharmacologically acceptable salt thereof according to claim 1, wherein $R^4$ represents a $C_{1-4}$ alkyl group and $R^5$ represents a hydrogen atom.

9. The anilide derivative or pharmacologically acceptable salt thereof according to claim 8, wherein $R^2$ represents a 3'-methyl group and $R^3$ represents a 5'-methyl group.

10. An antiarrhythmic agent comprising an excipient and the anilide derivative or pharamacologically acceptable salt thereof claimed in claim 8 or 9 as active ingredient.

11. The anilide derivative or pharmacologically acceptable salt thereof according to claim 1, wherein $R^2$ represents hydrogen atom and $R^3$ represents a hydrogen atom, a 3'-methyl group, a 3'-methoxy group or a 3'-methanesulfonamido group.

12. An antiarrhythmic agent comprising an excipient and the anilide derivative or pharmacologically acceptable salt thereof claimed in claim 11 as active ingredient.

13. The anilide derivative or pharmacologically acceptable salt thereof according to claim 1, wherein $R^2$ represents a 3'-methyl group and $R^3$ represents a 5'-methyl group.

14. An antiarrhythmic agent comprising an excipient and the anilide derivative or pharmacologically acceptable salt thereof claimed in claim 13 as active ingredient.

15. The anilide derivative represented by formula (1) or a pharmacologically acceptable salt thereof according to claim 1:

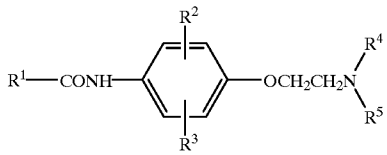

(1)

wherein
$R^1$ represents a substituted phenyl group selected from the group consisting of 2,6-di($C_{1-3}$alkoxy)phenyl groups, 2-($C_{1-3}$alkanesulfonamido)phenyl groups and a 2,6-dimethylphenyl group, $R^2$ and $R^3$ represent a hydrogen atom, respectively, $R^4$ represents a hydrogen atom or a $C_{1-3}$ alkyl group, a $C_{3-6}$ cycloalkyl group or —$(CH_2)_n OR^6$ (wherein n represents an integral number 2 or 3; and $R^6$ represents a $C_{1-3}$ alkyl group) and $R^5$ represents a hydrogen atom.

16. An antiarrhythmic agent comprising an excipient and the anilide derivative or pharmacologically acceptable salt thereof claimed in claim 15 as active ingredient.

17. An anilide derivative represented by formula (1) or a pharmacologically acceptable salt thereof:

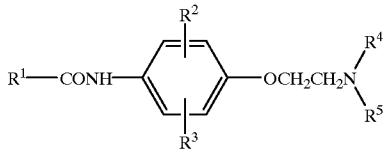

(1)

wherein
$R^1$ represents a substituted phenyl group selected from the group consisting of 2,6-di($C_{1-3}$ alkoxy)phenyl groups, 2-($C_{1-3}$alkanesulfonamido)phenyl groups and a 2,6-dimethylphenyl group;

$R^2$ and $R^3$ represent a hydrogen atom, respectively; and $R^4$ and $R^5$ represent independently a hydrogen atom or a $C_{1-3}$ alkyl group, a $C_{3-6}$ cycloalkyl group or —$(CH_2)_n$ $OR^6$ (wherein, n represents an integral number 2 or 3; and $R^6$ represents a $C_{1-3}$ alkyl group), or $R^4$ and $R^5$ together form —$(CH_2)_2W(CH_2)_2$— (wherein, W represents a direct bond, a methylene bridge or an oxygen atom).

18. An antiarrhythmic agent comprising an excipient and the anilide derivative or pharmacologically acceptable salt thereof claimed claim 17 as active ingredient.

19. The anilide derivative or pharmacologically acceptable salt thereof according to claim 1, wherein $R^1$ represents a 2,6-dimethoxyphenyl group, a 2,6-diethoxyphenyl group, a 2,6-dimethylphenyl group, a 2,6-diethylphenyl group, a phenyl group substituted with a $C_{1-3}$ alkanesulfonamido group at the 2-position, a 2-(methanesulfonyl)phenyl group, a furyl group, a 2,3,4,5-tetrahydrofuryl group, a 3,4,5,6-tetrahydro-2H-pyranyl group or —$(CH_2)_n OR^6$ (wherein, n represents an integral number 2 or 3 and $R^6$ represents a $C_{1-4}$ alkyl group.

20. The anilide derivative or pharmacologicallly acceptable salt thereof according to claim 1, wherein $R^1$ represents a 2,6-di($C_{1-3}$ alkoxy)phenyl group, a phenyl group substituted with a $C_{1-3}$ alkanesulfonamido group at the 2-position, a 2,6-dimethylphenyl group, a furyl group, a 2,3,4,5-tetrahydrofuryl group, a 3,4,5,6-tetrahydro-2H-pyranyl group or —$(HC_2)_n OR^6$ (wherein, n represents an integral number 2 or 3 and $R^6$ represents a $C_{1-4}$ alkyl group).

21. A method of treating atrial arrhythmia by administering an effective amount of an anilide derivative represented by formula (1) or a pharmacologically acceptable salt thereof:

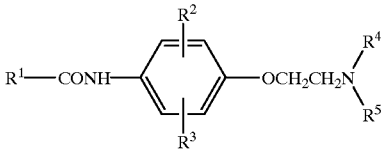

(1)

wherein
$R^1$ represents a phenyl group (except for monoalkoxy phenyl group) having one or two substituents selected from the group consisting of $C_{1-3}$ alkoxy groups, $C_{1-3}$ alkyl groups, $C_{1-3}$ alkanesulfonamido groups and $C_{1-3}$ alkanesulfonyl groups; a furyl group; a 2,3,4,5-tetrahydrofuryl group; a 3,4,5,6-tetrahydro-2H-pyranyl group; or —$(CH_2)_n OR^6$ (wherein, n represents an integral number 2 or 3 and $R^6$ represents a $C_{1-4}$ alkyl group), $R^2$ and $R^3$ represent independently a hydrogen atom, a $C_{1-3}$ alkoxy group, a $C_{1-3}$ alkyl group or a $C_{1-3}$ alkanesulfonamido group, $R^4$ and $R^5$ represent independently a hydrogen atom, a $C_{1-3}$ alkyl group, a $C_{3-6}$ cycloalkyl group or —$(CH_2)_n OR^6$ (wherein, n represents an integral number 2 or 3, $R^6$ represents a $C_{1-3}$ alkyl group), or $R^4$ and $R^5$ together form —$(CH_2)_2W(CH_2)_2$— (wherein, W represents a direct bond, a methylene bridge or an oxygen atom).

22. The method of treating atrial arrhythmia according to claim 21, wherein $R^2$ represents a 3'-methyl group, $R^3$ represents a 5'-methyl group, $R^4$ represents a $C_{1-3}$ alkyl group and $R^5$ represents a hydrogen atom.

23. The method of treating atrial arrhythmia according to claim 21 or 22, wherein the atrial arrhythmia is atrial flutter or atrial fibrillation.

24. The method of treating atrial arrhythmia according to claim 21, wherein $R^4$ represents a $C_{1-3}$ alkyl group and $R^5$ represents a hydrogen atom.

25. The method of treating atrial arrhythmia according to claim 24, wherein the atrial arrhythmia is atrial flutter or atrial fibrillation.

26. The method of treating atrial arrhythmia according to claim 21, wherein $R^2$ represents a hydrogen atom and $R^3$ represents a hydrogen atom, a 3'-methyl group, a 3'-methoxy group or a 3'-methanesulfonamido group.

27. The method of treating atrial arrhythmia according to claim 26, wherein the atrial arrhythmia is atrial flutter or atrial fibrillation.

28. The method of treating atrial arrhythmia according to claim 21, wherein $R^2$ represents a 3'-methyl group and $R^3$ represents a 5'-methyl group.

29. The method of treating atrial arrhythmia according to claim 28, wherein the atrial arrhythmia is atrial flutter or atrial fibrillation.

30. A method of treating atrial arrhythmia by administering an antiarrhythmic agent comprising an excipient and an anilide derivative represented by formula (1) or a pharmacologically acceptable salt thereof as an effective ingredient:

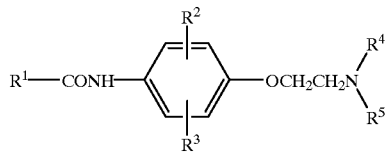

(1)

wherein $R^1$ represents a phenyl group (except for monoalkoxy phenyl group) having one or two substituents selected from the group consisting of $C_{1-3}$ alkoxy groups, $C_{1-3}$ alkyl groups, $C_{1-3}$ alkanesulfonamido groups and $C_{1-3}$ alkanesulfonyl groups; a furyl group; a 2,3,4,5-tetrahydrofuryl group; a 3,4,5,6-tetrahydro-2H-pyranyl group; or —$(CH_2)_nOR^6$ (wherein, n represents an integral number 2 or 3 and $R^6$ represents a $C_{1-3}$ alkyl group), $R^2$ and $R^3$ represent independently a hydrogen atom, a $C_{1-3}$ alkoxy group, a $C_{1-3}$ alkyl group, or a $C_{1-3}$ alkanesulfonamido group, $R^4$ and $R^5$ represent independently a hydrogen atom, a $C_{1-3}$ alkyl group, a $C_{3-6}$ cycloalkyl group, or —$(HC_2)_nOR^6$ (wherein, n represents an integral number 2 or 3, $R^6$ represents a $C_{1-3}$ alkyl group) or $R^4$ and $R^5$ together form —$(CH_2)_2W(CH_2)_2$— (wherein, W represents a direct bond, a methylene bridge or an oxygen atom).

31. The method of treating atrial arrhythmia according to claim 30, wherein the atrial arrhythmia is atrial flutter or atrial fibrillation.

* * * * *

UNITED STATES PATENT AND TRADEMARK OFFICE
CERTIFICATE OF CORRECTION

PATENT NO.   : 6,300,368 B1                                                         Page 1 of 1
DATED        : October 9, 2001
INVENTOR(S)  : Hiroyuki Yamashita et al.

It is certified that error appears in the above-identified patent and that said Letters Patent is hereby corrected as shown below:

<u>Title page,</u>
Item [73], should read as follows:
-- SCHERING AKTIENGESELLSCHAFT
Federal Republic of Germany --

<u>Column 29,</u>
Lines 40, 43 and 67, change "$C_{1-3}$" to -- $C_{1-4}$ --.

<u>Column 30,</u>
Lines 2, 42, 53, 55, 57, 60 and 66, change "$C_{1-3}$" to -- $C_{1-4}$ --;
Line 24, "-$(HC_2)_nOR^6$" to -- -$(CH_2)_nOR^6$ --;

<u>Column 32,</u>
Lines 12 and 21, change "$C_{1-3}$" to -- $C_{1-4}$ --.
Line 19, change "$C_{1-3}$" to -- $C_{1-4}$ --; change "-$(HC_2)_nOR^6$" to -- -$(CH_2)_nOR^6$ --;

Signed and Sealed this

Twelfth Day of November, 2002

Attest:

*Attesting Officer*

JAMES E. ROGAN
*Director of the United States Patent and Trademark Office*